(12) United States Patent
Shen et al.

(10) Patent No.: US 7,495,150 B2
(45) Date of Patent: Feb. 24, 2009

(54) METHOD OF INCREASING SEED OIL CONTENT IN PLANTS

(75) Inventors: Bo Shen, Johnston, IA (US); Mitchell C. Tarczynski, West Des Moines, IA (US)

(73) Assignee: Pioneer Hi-Bred International, Inc., Johnston, IA (US)

(*) Notice: Subject to any disclaimer, the term of this patent is extended or adjusted under 35 U.S.C. 154(b) by 480 days.

(21) Appl. No.: 11/147,109

(22) Filed: Jun. 7, 2005

(65) Prior Publication Data
US 2005/0278805 A1    Dec. 15, 2005

Related U.S. Application Data

(60) Provisional application No. 60/579,027, filed on Jun. 10, 2004.

(51) Int. Cl.
*C12N 15/82*    (2006.01)
(52) U.S. Cl. .................................. 800/281; 800/270
(58) Field of Classification Search .................. None
See application file for complete search history.

(56) References Cited

FOREIGN PATENT DOCUMENTS

WO    WO 02/22675 A2 *    3/2002

OTHER PUBLICATIONS

GenBank accession No. L32873 (GI: 1695243) submitted Nov. 1994.
GenBank accession No. Y178898 (GI: 5531483) submitted Aug. 1998.
GenBank accession No. ATU37589 (GI: 1173829) submitted Oct. 1995.
GenBank accession No. U85254 (GI: 1814423) submitted Jan. 1997.
GenBank accession No. U34743 (GI: 1173621) submitted Aug. 1995.
GenBank accession No. AAC80260 (GI: 1695244) submittted Nov. 1994.
GenBank accession No. CAB61059 (GI: 6434476) submitted Aug. 2001.
GenBank accession No. AAB49378 (GI: 1881536) submittted Oct. 1995.
GenBank accession No. AAB41901 (GI: 1814424) submitted Jan. 1997.
GenBank accession No. AAB37230 (GI: 1173622) submitted Aug. 1995.
Lu et al "Identification of a meristem L1 layer-specific gene in Arabidposis that is expressed during embryonic pattern formation and defines a new class of homeobox genes" The Plant Cell, vol. 8:2155-2168 (Dec. 1996).
Cristina et al. "The Arabidposis Athb-10 (GLABRA2) is an HD-Zip protein required for regulation of root hair development" The Plant Journal 10(3), 393-402 (1996).
Ingram et al. "ZmOCL1, an HDGL2 family homebox gene, is expressed in the outer cell layer throughout maize development" Plant Molecular Biology 40: 3430354 (1999).
Nadeau et al. "Ovule development: identification of stage-specific and tissue-specific cDNAs" The Plant Cell, vol. 8 213-239 (Feb. 1996).
Rerie et al. "The GLABRA2 gene encodes a homeo domain protein required for normal trichome development in Arabidopsis" Genes & Development 8:1388-1399 (1994).

* cited by examiner

*Primary Examiner*—Elizabeth F McElwain
(74) *Attorney, Agent, or Firm*—Patricia A. Sweeney

(57) ABSTRACT

Methods are provided for modulating seed oil content in plants. Specifically, the invention relates to methods of increasing seed oil content in plants by reducing or eliminating the expression of homeodomain glabara2 (HDGL2) in a plant of interest, or changing seed composition by increasing expression of HDGL2 in a plant. Seeds and plants produced by the present methods are also provided.

10 Claims, No Drawings

METHOD OF INCREASING SEED OIL CONTENT IN PLANTS

REFERENCE TO RELATED APPLICATION

This application claims benefit under 35 U.S.C.§119(e) of previously filed provisional application U.S. Ser. No. 60/579,027, filed Jun. 10, 2004, the entirety of which is incorporated by reference.

FIELD OF THE INVENTION

This invention relates generally to seed oil production in plants, and more specifically to methods of increasing plant seed oil content by altering expression of an HDGL2 gene in the plant, to compositions useful for practicing such methods, and to plants having increased seed oil content as compared to corresponding wild type plants.

BACKGROUND OF THE INVENTION

Oil is a major seed storage compound that has a great economic value for human nutrition, animal feed, and industrial applications.

Despite a detailed understanding of many aspects of the biosynthesis of fatty acid and storage lipid, and isolation of many genes in the pathways, the control mechanism for fatty acid biosynthesis and lipid accumulation in seed is not well understood.

Plant breeding studies have demonstrated that seed oil content can be increased significantly by selection. However, plant breeding procedures require a significant investment of time. Further, until a plant having the desired seed oil content is obtained, it cannot be known whether the selected plant will exhibit sufficient vigor. Thus, a need exists for convenient and predictable methods for producing plants that have a desired level of seed oil content.

SUMMARY OF THE INVENTION

The present invention is based, in part, on the discovery that mutation or down-regulation of a homeodomain glabra2 (HDGL2) family gene results in increased seed oil content in a plant. The HDGL2 gene family includes the *Arabidopsis thaliana* glabra2 gene, as well as orthologs of glabra2 such as the *Zea mays* ocl1 (Zmocl1) gene, the *Arabidopsis thaliana* meristem L1 (atml1) gene, the *Arabidopsis thaliana* homeodomain protein (ahdp) gene, and the *Phalaenopsis* sp. o39 gene, and encodes polypeptides having the characteristics of transcription factors. Based on this newly identified role of HDGL2 proteins in regulating seed oil production in plants, methods are provided for increasing seed oil content in plants by decreasing HDGL2 expression in cells of the plant. Also provided are plants that are genetically manipulated to have decreased levels of HDGL2 expression in cells of the plant, whereby the seed oil content of such plants is increased as compared to corresponding wild type plants. Increasing of expression of HDGL2 is also provided.

DETAILED DESCRIPTION OF THE INVENTION

The present invention is drawn to methods for increasing seed oil content in a plant. Homeobox genes such as the HDGL2 genes encode polypeptides that act as transcription factors and generally are involved in developmental programming of an organism. As disclosed herein, homeobox genes encoding HDGL2 family members also have a role in seed oil accumulation in plants. Accordingly, the present invention provides methods of increasing seed oil production in a plant by genetically manipulating HDGL2 gene expression. The invention further provides plants or parts of a plant that are genetically modified to reduce or eliminate the expression of HDGL2, wherein the seeds of such plants are characterized, in part, in producing greater amounts of seed oil as compared to corresponding wild type plants.

In seeds, oil is accumulated as triacylglycerols (TAGs) which are synthesized from glycerol-3-phosphate and fatty acyl-CoA in the endoplasmic reticulum. Fatty acid is synthesized from acetyl-CoA exclusively in the plastid and transported to cytoplasm in the form of fatty acyl-CoA. In the endoplasmic reticulum, TAGs are synthesized by the stepwise acylation of the glycerol-3-phosphate known as Kennedy pathway. First, the fatty acyl moieties were added to the sn-1 and sn-2 positions of glycerol-3-phosphate respectively by glycerol-3-phosphate acyltransferase and lysophosphatidic acid acyltransferase to form phosphatidic acid. Phosphatidic acid is then hydrolyzed by phosphatidate phosphahydrase to yield diacylglycerol (DAG). DAG can be used to form TAGs or to enter membrane lipid synthesis. Finally, diacylglycerol acyltransferase, the only enzyme specific to TAG synthesis, adds a third acyl chain to DAG and yields TAGs. Alternative pathways for TAG synthesis may also exit in plants. TAGs are then stored in seeds in the form of oil bodies as energy reserve for seed germination.

In vitro feeding studies indicated that supply of fatty acid is one limiting factor for oil accumulation in developing embryo. Acetyl CoA carboxylase (ACCase), the first enzyme in fatty acid synthesis, is considered to be a control point for carbon flux into fatty acid synthesis. Expression of *Arabidopsis* cytosolic ACCase in *B. napus* resulted in a 5% increase in seed oil content. However, overexpression of other key enzymes in the fatty acid synthesis pathway, including LAS I, KAS II, and KAS III, did not lead to an increase in seed oil content in plants. Other studies indicated that TAG synthesis could be a limiting factor for oil accumulation. Expression of yeast sn-2 acyltransferase in Brassicaceae increased seed oil content by 20%, and overexpression of DGAT in *Arabidopsis* also resulted in an 11-28% increase in seed oil.

More recently, metabolic flux control analysis indicated that there is no single major control step in the pathway; approximately 60% of control is exerted by fatty acid synthesis, while 40% of control is exerted by TAG synthesis. These results suggest that manipulation of a single step in the overall pathway is not likely to have much effect on storage lipid accumulation in seed.

For example, following 28 cycles of selection, maize kernel oil reached 20% in a high oil ASK line as compared to the starting line, which had 4% kernel oil. The increase in oil accumulation is mainly observed in the maize embryo, which serves as the primary organ for oil accumulation and deposition. The maize endosperm, which constitutes the bulk of the kernel, contains the majority of storage proteins and starch in the kernel and is not typically regarded as an oil storage site.

The HDGL2 gene family is named after the *A. thaliana* glabra2 gene, which was identified as encoding a homeodomain protein involved in trichome development in *Arabidopsis* (Rerie et al. (1994) *Genes Devel.* 8:1388-1399; see, also, Lu et al. (1996) *Plant Cell* 8:2155-2168, each of which is incorporated herein by reference). The HDGL2 genes encode polypeptides that have a homeodomain-leucine zipper (HD-Zip) domain, which is characteristic of transcription factors (see, e.g., Di Cristina et al. (1996) *Plant J.* 10:393-402, which is incorporated herein by reference). Additionally, the HDGL2 gene encodes a START domain (Ingram et al. (1999)

*Plant Mol. Biol.* 40:343-354, which is incorporated herein by reference). The HDGL2 gene family includes orthologs of glabra2 such as the *Zea mays* ocl1 (Zmocl1) gene (Ingram et al. (1999) supra), the *A. thaliana* meristem L1 (atml1) gene (Lu et al. (1996) supra), the *A. thaliana* homeodomain protein (ahdp) gene (Lu et al. (1996) supra), and the *Phalaenopsis* o39 gene (Nadeau et al. (1996) *Plant Cell* 8:213-239, which is incorporated herein by reference).

Nucleotide and amino acid sequences of representative HDGL2 family members are exemplified herein. Exemplary nucleotide sequences (genomic or cDNA) include, but are not limited to, glabra2 (SEQ ID NO:1; GenBank Acc. No. L32873), Zmocl1 (SEQ ID NO:3; GenBank Acc. No. Y17898; see, also, FIG. 5A), atml1 (SEQ ID NO:5; GenBank Acc. No. U37589), ahdp (SEQ ID NO:7; GenBank Acc. No. U85254), and o39 (SEQ ID NO:9; GenBank Acc. No. U34743), each of which is incorporated herein by reference. Exemplary amino acid sequences include, but are not limited to, GLABRA2 (SEQ ID NO:2; GenBank Acc. No. MC80260), Zmocl1 (SEQ ID NO:4; GenBank Acc. No. CAB51059; see, also, FIG. 5B), ATML1 (SEQ ID NO:6; GenBank Acc. No. AAB49378), AHDP (SEQ ID NO:8; GenBank Acc. No. MB41901), and O39 (SEQ ID NO:10; GenBank Acc. No. MB37230), each of which is incorporated herein by reference. It will be recognized that the exemplified HDGL2 nucleotide and amino acid sequences can be used to search a database to identify additional HDGL2 family homologs and orthologs (e.g., Zmocl2, Zmocl3 and Zmocl4), and that such homologs and orthologs can be useful for preparing compositions and practicing methods of the invention.

In some embodiments, HDGL2 expression is reduced or eliminated by transforming a plant cell with an expression cassette that expresses a polynucleotide that inhibits the expression of HDGL2. Methods for reducing or eliminating the expression of a gene in a plant are well known in the art, and any such method may be used in the present invention to inhibit the expression of one or more HDGL2s.

In accordance with the present invention, the expression of HDGL2 is reduced if the protein or transcript level of HDGL2 is less than 70% of the protein or transcript level of the same HDGL2 in a plant that has not been genetically modified or mutagenized to inhibit the expression of that HDGL2. In particular embodiments of the invention, the protein or transcript level of the HDGL2 in a modified plant according to the invention is less than 60%, less than 50%, less than 40%, less than 30%, less than 20%, less than 10%, or less than 5% of the protein or transcript level of the same HDGL2 in a plant that is not a mutant or that has not been genetically modified to inhibit the expression of that HDGL2. The expression level of HDGL2 may be measured, for example, by assaying for the level of HDGL2 protein or transcript in the plant cells. The expression of HDGL2 is "eliminated" according to the invention when it is not detectable by at least one assay method.

In other embodiments, the expression of HDGL2 may be reduced or eliminated by disrupting the gene encoding HDGL2. The invention encompasses mutagenized plants that carry mutations in HDGL2 genes, where the mutations reduce or eliminate the expression of HDGL2.

Thus, many methods may be used to reduce or eliminate the expression of HDGL2. More than one method may be used to reduce the expression of one HDGL2. In addition, combinations of methods may be employed to reduce or eliminate the expression of different HDGL2s.

Non-limiting examples of methods of reducing or eliminating the expression of a HDGL2 are given below.

In some embodiments of the present invention, a plant cell is transformed with an expression cassette that is capable of expressing a polynucleotide that inhibits the expression of HDGL2. The term "expression" as used herein refers to the biosynthesis of a gene product, including the transcription and/or translation of said gene product. For example, for the purposes of the present invention, an expression cassette capable of expressing a polynucleotide that inhibits the expression of at least one HDGL2 is an expression cassette capable of producing an RNA molecule that inhibits the transcription and/or translation of at least one HDGL2. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an HDGL2 are given below.

In some embodiments of the invention, inhibition of the expression of HDGL2 may be obtained by sense suppression or cosuppression. For cosuppression, an expression cassette is designed to express an RNA molecule corresponding to all or part of a messenger RNA encoding an HDGL2 in the "sense" orientation. Overexpression of the RNA molecule can result in reduced expression of the native gene. Accordingly, multiple plant lines transformed with the cosuppression expression cassette are screened to identify those that show the greatest inhibition of HDGL2 expression.

The polynucleotide used for cosuppression may correspond to all or part of the sequence encoding the HDGL2, all or part of the 5' and/or 3' untranslated region of an HDGL2 transcript, or all or part of both the coding sequence and the untranslated regions of a transcript encoding HDGL2. That is, a polynucleotide used for cosuppression or other gene silencing methods may share 99%, 98%, 97%, 96%, 95%, 94%, 93%, 92%, 91%, 90%, 89%, 88%, 87%, 85%, 80%, or less sequence identity with the target sequence. When portions of the polynucleotides are used to disrupt the expression of the target gene, generally, sequences of at least 15, 20, 30, 35, 40, 45, 50, 60, 70, 80, 90, 100, 200, 300, 400, 450, 500, 550, 600, 650, 700, 750, 800, or 900 nucleotides or 1 kb or greater may be used. In some embodiments where the polynucleotide comprises all or part of the coding region for the HDGL2, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin et al. (2002) *Plant Cell* 14: 1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell et al. (1994) *Proc. Natl. Acad. Sci. USA* 91: 3490-3496; Jorgensen et al. (1996) *Plant Mol. Biol.* 31: 957-973; Johansen and Carrington (2001) *Plant Physiol.* 126: 930-938; Broin et al. (2002) *Plant Cell* 14: 1417-1432; Stoutjesdijk et al (2002) *Plant Physiol.* 129: 1723-1731; Yu et al. (2003) *Phytochemistry* 63: 753-763; and U.S. Pat. Nos. 5,034,323, 5,283,184, and 5,942,657, each of which is herein incorporated by reference. The efficiency of cosuppression may be increased by including a poly-dT region in the expression cassette at a position 3' to the sense sequence and 5' of the polyadenylation signal. See, e.g., U.S. Patent Publication No. 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323, herein incorporated by reference.

In some embodiments of the invention, inhibition of the expression of the HDGL2 may be obtained by antisense suppression. For antisense suppression, the expression cassette is designed to express an RNA molecule complementary to all or part of a messenger RNA encoding the HDGL2. Overexpression of the antisense RNA molecule can result in reduced expression of the endogenous gene. Accordingly, multiple plant lines transformed with the antisense suppression expression cassette are screened to identify those that show the greatest inhibition of HDGL2 expression.

The polynucleotide for use in antisense suppression may correspond to all or part of the complement of the sequence encoding the HDGL2, all or part of the complement of the 5' and/or 3' untranslated region of the HDGL2 transcript, or all or part of the complement of both the coding sequence and the untranslated regions of a transcript encoding the HDGL2. In addition, the antisense polynucleotide may be fully complementary (i.e., 100% identical to the complement of the target sequence) or partially complementary (i.e., less than 100% identical to the complement of the target sequence) to the target sequence. That is, an antisense polynucleotide may share 99%, 98%, 97%, 96%, 95%, 94%, 93%, 92%, 91%, 90%, 89%, 88%, 87%, 85%, 80%, or less sequence identity with the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 30, 40, 50, 60, 70, 80, 90, 100, 200, 300, 400, 450, 500, or 550 nucleotides or greater may be used.

Methods for using antisense suppression to inhibit the expression of endogenous genes in plants are described, for example, in Liu et al (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020048814, herein incorporated by reference.

In some embodiments of the invention, inhibition of the expression of an HDGL2 may be obtained by doublestranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of HDGL2 expression. Methods for using dsRNA interference to inhibit the expression of endogenous plant genes are described in Waterhouse et al. (1998) *Proc. Natl. Acad. Sci. USA* 95: 13959-13964, Liu et al. (2002) *Plant Physiol.* 129: 1732-1743, and WO 99/49029, WO 99/53050, WO 99/61631, and WO 00/49035; each of which is herein incorporated by reference.

In some embodiments of the invention, inhibition of the expression of one or more HDGL2s may be obtained by hairpin RNA (hpRNA) interference or intron-containing hairpin RNA (ihpRNA) interference. These methods are highly efficient at inhibiting the expression of endogenous genes. See, Waterhouse and Helliwell (2003) *Nat. Rev. Genet.* 4: 29-38 and the references cited therein. These methods can make use of either coding region sequences or promoter or regulatory region sequences.

For hpRNA interference, the expression cassette is designed to express an RNA molecule that hybridizes with itself to form a hairpin structure that comprises a singlestranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97: 4985-4990; Stoutjesdijk et al. (2002) *Plant Physiol.* 129: 1723-1731; and Waterhouse and Helliwell (2003) *Nat. Rev. Genet.* 4: 29-38. Methods for using hpRNA interference to inhibit or silence the expression of genes are described, for example, in Chuang and Meyerowitz (2000) *Proc. Natl. Acad. Sci. USA* 97: 4985-4990; Stoutjesdijk et al. (2002) *Plant Physiol.* 129: 1723-1731; Waterhouse and Helliwell (2003) *Nat. Rev. Genet.* 4: 29-38; Pandolfini et al. BMC Biotechnology 3: 7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30: 135-140, herein incorporated by reference. The loop region may vary in length. Thus, the loop region may be at least 100, 200, 300, 400, 500, 600, 700, 800, 900 nucleotides in length, or at least 1, 2, 3, 4, 5, 6, 7, 8, 9, or 10 kb in length.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith et al. (2000) *Nature* 407: 319-320. In fact, Smith et al. show 100% suppression of endogenous gene expression using ihpRNA-mediated interference. Methods for using ihpRNA interference to inhibit the expression of endogenous plant genes are described, for example, in Smith et al. (2000) *Nature* 407:319-320; Wesley et al. (2001) *Plant J.* 27: 581-590; Wang and Waterhouse (2001) *Curr. Opin. Plant Biol.* 5: 146-150; Waterhouse and Helliwell (2003) *Nat. Rev. Genet.* 4: 29-38; Helliwell and Waterhouse (2003) *Methods* 30: 289-295, and U.S. Patent Publication No. 20030180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for HDGL2). Methods of using amplicons to inhibit the expression of endogenous plant genes are described, for example, in Angell and Baulcombe (1997) *EMBO J.* 16: 3675-3684, Angell and Baulcombe (1999) *Plant J.* 20: 357-362, and U.S. Pat. No. 6,646,805, each of which is herein incorporated by reference.

In some embodiments, the polynucleotide expressed by the expression cassette of the invention is catalytic RNA or has ribozyme activity specific for the messenger RNA of HDGL2. Thus, the polynucleotide causes the degradation of the endogenous messenger RNA, resulting in reduced expression of the HDGL2. This method is described, for example, in U.S. Pat. No. 4,987,071, herein incorporated by reference.

In some embodiments of the invention, inhibition of the expression of one or more HDGL2s may be obtained by RNA interference by expression of a gene encoding a micro RNA (mRNA). mRNAs are regulatory agents consisting of about 22 ribonucleotides. mRNAs are highly efficient at inhibiting the expression of endogenous genes. See, for example, Javier et al. (2003) *Nature* 425: 257-263, herein incorporated by reference.

For mRNA interference, the expression cassette is designed to express an RNA molecule that is modeled on an endogenous mRNA gene. The mRNA gene encodes an RNA that forms a hairpin structure containing a 22-nucleotide sequence that is complementary to another endogenous gene (target sequence). For suppression of HDGL2 expression, the 22-nucleotide sequence is selected from an HDGL2 transcript sequence and contains 22 nucleotides of said HDGL2 sequence in sense orientation and 21 nucleotides of a corresponding antisense sequence that is complementary to the sense sequence. mRNA molecules are highly efficient at inhibiting the expression of endogenous genes, and the RNA interference they induce is inherited by subsequent generations of plants.

In some embodiments of the present invention, the expression of HDGL2 is reduced or eliminated by disrupting the gene encoding the HDGL2. The gene encoding the HDGL2 may be disrupted by any method known in the art. For example, in one embodiment, the gene is disrupted by transposon tagging. In another embodiment, the gene is disrupted by mutagenizing maize plants using random or targeted mutagenesis, and selecting for plants that have reduced levels of HDGL2 expression.

In one embodiment of the invention, transposon tagging is used to reduce or eliminate the expression of one or more HDGL2s. Transposon tagging comprises inserting a transposon within an endogenous HDGL2 gene to reduce or eliminate expression of the HDGL2. "HDGL2 gene" is intended to mean the gene that encodes a HDGL2 protein according to the invention.

In this embodiment, the expression of one or more HDGL2s is reduced or eliminated by inserting a transposon within a regulatory region or coding region of the gene encoding the HDGL2. A transposon that is within an exon, intron, 5' or 3' untranslated sequence, a promoter, or any other regulatory sequence of an HDGL2 gene may be used to reduce or eliminate the expression of the encoded HDGL2.

Methods for the transposon tagging of specific genes in plants are well known in the art. See, for example, Maes et al. (1999) *Trends Plant Sci.* 4: 90-96; Dharmapuri and Sonti (1999) *FEMS Microbiol. Lett.* 179: 53-59; Meissner et al. (2000) *Plant J.* 22: 265-274; Phogat et al. (2000) *J. Biosci.* 25: 57-63; Walbot (2000) *Curr. Opin. Plant Biol.* 2: 103-107; Gai et al. (2000) *Nucleic Acids Res.* 28: 94-96; Fitzmaurice et al. (1999) *Genetics* 153: 1919-1928. In addition, the TUSC process for selecting Mu insertions in selected genes has been described in Bensen et al. (1995) *Plant Cell* 7: 75-84; Mena et al. (1996) *Science* 274: 1537-1540; and U.S. Pat. No. 5,962,764; each of which is herein incorporated by reference.

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see Ohshima et al. (1998) *Virology* 243: 472-481; Okubara et al. (1994) *Genetics* 137: 867-874; and Quesada et al. (2000) *Genetics* 154: 421436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See McCallum et al. (2000) *Nat. Biotechnol.* 18: 455-457, herein incorporated by reference.

In another embodiment of this invention, dominant mutants can be used to trigger RNA silencing due to gene inversion and recombination of a duplicated gene locus. See, for example, Kusaba et al. (2003) *Plant Cell* 15: 1455-1467.

The invention encompasses additional methods for reducing or eliminating the expression of one or more HDGL2s. Examples of other methods for altering or mutating a genomic nucleotide sequence in a plant are known in the art and include, but are not limited to, the use of chimeric vectors, chimeric mutational vectors, chimeric repair vectors, mixed-duplex oligonucleotides, self-complementary oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,984; each of which are herein incorporated by reference. See also, WO 98/49350, WO 99/07865, WO 99/25821, and Beetham et al. (1999) *Proc. Natl. Acad. Sci. USA* 96: 8774-8778; each of which is herein incorporated by reference. Other methods of suppressing expression of a gene involve promoter-based silencing. See, for example, Mette et al. (2000) *EMBO J.* 19: 5194-5201; Sijen et al. (2001) *Curr. Biol.* 11: 436-440; Jones et al. (2001) *Curr. Biol.* 11: 747-757.

Where polynucleotides are used to decrease or inhibit the expression of HDGL2, it is recognized that modifications of the exemplary sequences disclosed herein may be made as long as the sequences act to decrease or inhibit expression of the corresponding mRNA. Thus, for example, polynucleotides having at least about 70%, 80%, 85%, 86%, 87%, 88%, 89%, 90%, 91%, 92%, 93%, 94%, 95%, 96%, 97%, 98%, 99%, or 100% sequence identity to the exemplary sequences disclosed herein may be used. Furthermore, portions or fragments of the exemplary sequences or portions or fragments of polynucleotides sharing a particular percent sequence identity to the exemplary sequences may be used to disrupt the expression of the target gene. Generally, sequences of at least 10, 15, 20, 25, 30, 35, 40, 45, 50, 60, 70, 80, 90, 100, 120, 140, 160, 180, 200, 220, 240, 250, 260, 280, 300, 350, 400, 450, 500, 600, 700, 800, 900, 1000, or more nucleotides, or greater may be used. It is recognized that in particular embodiments, the complementary sequence of such sequences may be used. For example, hairpin constructs comprise both a sense and a complementary, or antisense, portion or fragment corresponding to the gene of interest. Antisense constructs may share less than 100% sequence identity with the gene of interest, and may comprise portions or fragments of the gene of interest, so long as the object of the embodiment is achieved, i.e., so long as expression of the gene of interest is decreased.

In another embodiment of the invention, overexpression of the HDGL2 gene may be accomplished. In this embodiment, an expression cassette is created capable of expressing a polynucleotide that results in increased expression of at least one HDGL2. This will impact composition of the seed, which may be desired in any of a number of applications, such as where decreased seed oil content, increased starch content, or the like is the goal. As discussed in more detail below, this can include optimization of the gene(s) for increased expression in the plant, sequence modification that enhance gene expression such as elimination of sequences encoding spurious polyadenylation signals, exon-intron splice site signals, transposon-like repeats, and other such well-characterized sequences that may be deleterious to gene expression. Adjustment of the G-C content of the sequence to levels average for a given cellular host, and modification of the sequence to avoid predicted hairpin secondary mRNA structures can also be employed, as well as use of 5' leader sequences and introns.

Plant transformants containing a desired genetic modification as a result of any of the above described methods resulting in increased, decreased or eliminated expression can be selected by various methods known in the art. These methods include, but are not limited to, methods such as SDS-PAGE analysis, immunoblotting using antibodies which bind to the seed protein of interest, single nucleotide polymorphism (SNP) analysis, or assaying for the products of a reporter or marker gene, and the like.

It is recognized that the methods of the invention may employ a nucleotide construct that is capable of directing, in a transformed plant, the expression of at least one protein, or the transcription of at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or transcription of an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

By "modulating" or "modulate" as used herein is intended that the level or amount of a product is increased or decreased in accordance with the goal of the particular embodiment. For example, if a particular embodiment were useful for producing purified HDGL2 protein, it would be desirable to increase the amount of HDGL2 protein expressed. By "expression" is generally intended the translation of a particular mRNA into a protein; however, in some contexts, "expression" refers to the overall process of production of a protein and therefore includes both transcription of an mRNA and translation of the corresponding protein.

Fragments and variants of the disclosed polynucleotides and proteins encoded thereby are also encompassed by the present invention. By "fragment" is intended a portion of the polynucleotide or a portion of the nucleotide sequence and hence protein encoded thereby, if any. Fragments of a nucleotide sequence may encode protein fragments that retain the biological activity of the native protein and hence have HDGL2 transcriptional factor activity. Alternatively, fragments of a nucleotide sequence that are useful as hybridization probes or in sense or antisense suppression generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of an HDGL2 nucleotide sequence that encodes a biologically active portion of a HDGL2 protein of the invention will encode at least 15, 25, 30, 50, 100, 150, 200, 250, 300, 350, 400, 450, 500, 550, 600, 650, 700, 750, 800, 850, 900, 950, 1000, 1100, 1200, 1300, 1400, or 1500 contiguous amino acids, or up to the total number of amino acids present in a full-length HDGL2 protein of the invention (for example, 784 amino acids for SEQ ID NO: 4). Fragments of an HDGL2 nucleotide sequence that are useful in non-coding embodiments, for example, as PCR primers or for sense or antisense suppression, generally need not encode a biologically active portion of an HDGL2 protein. Thus it will be appreciated that a fragment of an HDGL2 polypeptide of the invention will similarly contain at least 15, 25, 30, 50, 100, 150, 200, 250, 300, 350, 400, 450, 500, 550, 600, 650, 700, or 750 contiguous amino acids, or up to the total number of amino acids present in a full-length HDGL2 protein of the invention (for example, 784 amino acids for SEQ ID NO: 4).

Thus, a fragment of an HDGL2 nucleotide sequence may encode a biologically active portion of an HDGL2 protein, or it may be a fragment that can be used, for example, as a hybridization probe or in sense or antisense suppression using methods disclosed herein and known in the art. A biologically active portion of an HDGL2 protein can be prepared by isolating a portion of one of the HDGL2 polynucleotides of the invention, expressing the encoded portion of the HDGL2 protein (e.g., by recombinant expression in vitro), and assessing the activity of the encoded portion of the HDGL2 protein. Nucleic acid molecules that are fragments of an HDGL2 polynucleotide comprise at least 16, 20, 50, 75, 100, 150, 200, 250, 300, 350, 400, 450, 500, 550, 600, 650, 700, 800, 900, 1,000, 1,100, 1,200, 1,300, 1,400, 1,500, 1,600, 1,700, 1,800, 1,900, 2,000, or 3,000 nucleotides, or up to the number of nucleotides present in a full-length MRP polynucleotide disclosed herein (for example, 3072 nucleotides for SEQ ID NO: 3).

By "variants" is intended substantially similar sequences. For nucleotide sequences, conservative variants include those sequences that, because of the degeneracy of the genetic code, encode the amino acid sequence of one of the MRP polypeptides of the invention, or a portion thereof. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode an HDGL2 protein of the invention, or a portion thereof. Generally, variants of a particular nucleotide sequence of the invention will have at least about 40%, 45%, 50%, 55%, 60%, 65%, 70%, 75%, 80%, 85%, 90%, 91%, 92%, 93%, 94%, 95%, 96%, 97%, or at least about 98%, 99% or more sequence identity to that particular nucleotide sequence as determined by sequence alignment programs described elsewhere herein using default parameters.

Variants of a particular polynucleotide of the invention (i.e., variants of the reference nucleotide sequence) can also be evaluated by comparison of the percent sequence identity between the polypeptide encoded by a variant nucleotide sequence and the polypeptide encoded by the reference nucleotide sequence. Percent sequence identity between any two polypeptides can be calculated using sequence alignment programs described elsewhere herein using default parameters. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, generally at least about 75%, 80%, 85%, at least about 90%, 91%, 92%, 93%, 94%, 95%, 96%, 97%, or at least about 98%, 99% or more sequence identity.

For polynucleotides, a variant comprises a deletion and/or addition at one or more nucleotides at one or more internal sites within the native polynucleotide and/or a substitution of one or more nucleotides at one or more sites in the native polynucleotide. As used herein, a "native" polypeptide or polynucleotide comprises a naturally occurring amino acid sequence or nucleotide sequence. For polynucleotides, conservative variants include those sequences that, because of the degeneracy of the genetic code, encode the amino acid sequence of one of the polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode an HDGL2 protein of the invention. Generally, variants of a particular polynucleotide of the invention will have at least about 40%, 45%, 50%, 55%, 60%, 65%, 70%, 75%, 80%, 85%, 87%, 90%, 91%, 92%, 93%, 94%, 95%, 96%, 97%, 98%, 99% or more sequence identity to that particular polynucleotide as determined by sequence alignment programs and parameters described elsewhere herein.

"Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they continue to possess the desired biological activity of the native protein. Such variants may result from, for example, genetic polymorphism or from human manipulation. Biologically active variants of a native HDGL2 protein of the invention will have at least about 40%, 45%, 50%, 55%, 60%, 65%, 70%, 75%, 80%, 85%, 87%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the proteins can be prepared by the creation of mutations in the DNA. Methods for mutagenesis and nucleotide sequence alterations are well known in the art. See, for example, Kunkel (1985) *Proc. Natl. Acad. Sci. USA* 82: 488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Nat'l. Biomed. Res. Found., Washington, D.C.), herein incorporated by reference. Conservative substitutions, such as exchanging one amino acid with another having similar properties, may be made.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired HDGL2 transcriptional factor activity. Obviously, the mutations that will be made in the DNA encoding the variant must not place the sequence out of reading frame and preferably will not create complementary regions that could produce secondary mRNA structure. See, EP Patent Application Publication No. 75,444.

Variant polynucleotides and proteins also encompass sequences and proteins derived from a mutagenic and recombinogenic procedure such as DNA shuffling. With such a procedure, one or more different HDGL2 coding sequences can be manipulated to create a new HDGL2 possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the HDGL2 gene of the invention and other known HDGL2 genes to obtain a new gene coding for a protein with an improved property of interest. Strategies for such DNA shuffling are known in the art. See, for example, Stemmer (1994) *Proc. Natl. Acad. Sci. USA* 91: 10747-10751; Stemmer (1994) *Nature* 370: 389-391; Crameri et al. (1997) *Nature Biotech.* 15: 436-438; Moore et al., (1997) *J. Mol. Biol.* 272: 336-347; Zhang et al. (1997) *Proc. Natl. Acad. Sci. USA* 94: 4504-4509; Crameri et al., (1998) *Nature* 391: 288-291; and U.S. Pat. Nos. 5,605,793 and 5,837,458.

The present invention further provides a method for modulating (i.e., increasing or decreasing) the concentration or composition of the polypeptides of the claimed invention in a plant or part thereof. Modulation can be effected by increasing or decreasing the concentration and/or the composition (i.e., the ratio of the polypeptides of the claimed invention) in a plant.

In some embodiments, the method comprises transforming a plant cell with a cassette comprising a polynucleotide of the invention to obtain a transformed plant cell, growing the transformed plant cell under conditions allowing expression of the polynucleotide in the plant cell in an amount sufficient to modulate concentration and/or composition of the corresponding protein in the plant cell. In some embodiments, the method comprises utilizing the polynucleotides of the invention to create a deletion or inactivation of the native gene. Thus, a deletion may constitute a functional deletion, i.e., the creation of a "null" mutant, or it may constitute removal of part or all of the coding region of the native gene. Methods for creating null mutants are well-known in the art and include, for example, chimeraplasty. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

In addition to sense and antisense suppression, catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al. (1988) *Nature* 334: 585-591.

A variety of cross-linking agents, alkylating agents and radical-generating species as pendant groups on polynucleotides of the present invention can be used to bind, label, detect, and/or cleave nucleic acids. For example, Vlassov et al. (1986) *Nucl. Acids Res.* 14: 4065-4076 describes covalent bonding of a single-stranded DNA fragment with alkylating derivatives of nucleotides complementary to target sequences. Similar work is reported in Knorre et al. (1985) *Biochimie* 67: 785-789. Others have also showed sequence-specific cleavage of single-stranded DNA mediated by incorporation of a modified nucleotide which was capable of activating cleavage (Iverson and Dervan (1987) *J. Am. Chem. Soc.* 109: 1241-1243). Meyer et al. ((1989) *J. Am. Chem. Soc.* 111: 8517-8519) demonstrated covalent crosslinking to a target nucleotide using an alkylating agent complementary to the single-stranded target nucleotide sequence. Lee et al. ((1988) *Biochemistry* 27: 3197-3203) disclosed a photoactivated crosslinking to single-stranded oligonucleotides mediated by psoralen. Home et al. ((1990) *J. Am Chem. Soc.* 112: 2435-2437) used crosslinking with triple-helix-forming probes. Webb and Matteucci ((1986) *J. Am. Chem. Soc.* 108: 2764-2765) and Feteritz et al. ((1991) *J. Am. Chem. Soc.* 113: 4000) used N4, N4-ethanocytosine as an alkylating agent to crosslink to single-stranded oligonucleotides. In addition, various compounds to bind, detect, label, and/or cleave nucleic acids are known in the art. See, for example, U.S. Pat. Nos. 5,543,507; 5,672,593; 5,484,908; 5,256,648; and 5,681, 941. Such embodiments are collectively referred to herein as "chemical destruction."

In some embodiments, an isolated nucleic acid (e.g., a vector) comprising a promoter sequence is transfected into a plant cell. Subsequently, a plant cell comprising the promoter operably linked to a nucleic acid or polynucleotide comprising a nucleotide sequence of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant-forming conditions for a time sufficient to modulate the concentration and/or composition of polypeptides of the present invention in the plant. Plant forming conditions are well known in the art.

In general, when an endogenous polypeptide is modulated using the methods of the invention, the content of the polypeptide in a plant or part or cell thereof is increased or decreased by at least 5%, 10%, 20%, 30%, 40%, 50%, 60%, 70%, 80%, 90%, or more relative to a native control plant, plant part, or cell lacking the aforementioned cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation.

The polynucleotides disclosed herein can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire HDGL2 sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated sequences that encode an HDGL2 protein which hybridize under stringent conditions to the HDGL2 sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York).

Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other nucleic acids comprising corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the HDGL2 sequences disclosed herein. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire HDGL2 sequences disclosed herein, or one or more portions thereof, may be used as probes capable of specifically hybridizing to corresponding HDGL2 sequences and messenger RNAs. To achieve specific hybridization under a variety of conditions, such probes include sequences that are unique among HDGL2 sequences and are at least about 10, 12, 15, 16, 17, 18, 19, 20, 21, 22, 23, 24, 25, or 30 nucleotides in length. Such probes may be used to amplify corresponding HDGL2 sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 or 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, "% form" is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.). The duration of the wash time will be at least a length of time sufficient to reach equilibrium.

The following terms are used to describe the sequence relationships between two or more nucleic acids or polynucleotides: (a) "reference sequence", (b) "comparison window", (c) "sequence identity", and (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, or 100 nucleotides in length, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4: 11-17; the local alignment algorithm of Smith et al. (1981) *Adv. Appl. Math.* 2: 482; the global alignment algorithm of Needleman and Wunsch (1970) *J. Mol. Biol.* 48: 443-453; the search-for-local-alignment-method of Pearson and Lipman (1988) *Proc. Natl. Acad. Sci.* 85: 2444-2448; the algorithm of Karlin and Altschul (1990) *Proc. Natl. Acad. Sci. USA* 87: 2264, modified as in Karlin and Altschul (1993) *Proc. Natl. Acad. Sci. USA* 90: 5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73: 237-244 (1988); Higgins et al. (1989) *CABIOS* 5: 151-153; Corpet et al. (1988) *Nucleic Acids Res.* 16: 10881-90; Huang et al. (1992) *CABIOS* 8: 155-65; and Pearson et al. (1994) *Meth. Mol. Biol.* 24: 307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215: 403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25: 3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nim.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2; and the BLOSUM62 scoring matrix or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The HDGL2 polynucleotide of the invention can be provided in expression cassettes for expression in the plant of interest. The cassette will include 5' and 3' regulatory sequences operably linked to an HDGL2 polynucleotide of the invention. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, "operably linked" is intended to mean that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the HDGL2 polynucleotide to be under the transcriptional regulation of the regulatory regions. The expression cassette may additionally contain selectable marker genes.

Such a cassette is provided with a plurality of restriction sites and/or recombination sites for insertion of the coding sequence to be under the transcriptional control of the regulatory regions. The cassette may additionally contain selectable marker genes. If protein expression is desired, the cassette may be referred to as a protein expression cassette and will include in the 5'-3' direction of transcription: a transcriptional and translational initiation region (i.e., a promoter), an HDGL2 nucleotide sequence of the invention, and a transcriptional and translational termination region (i.e., termination region) functional in plants.

The regulatory regions (i.e., promoters, transcriptional regulatory regions, and translational termination regions) and/or the HDGL2 polynucleotide of the invention may be native/analogous to the host cell or to each other. Alternatively, the regulatory regions and/or the HDGL2 polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from that from which the polynucleotide was derived, or, if from the same/analogous species, one or both are substantially modified from their original form, or the promoter is not the native promoter for the operably linked polynucleotide.

While it may be optimal to express the sequences using heterologous promoters, the native promoter sequences may be used. Such constructs can change expression levels of HDGL2 in the plant or plant cell. Thus, the phenotype of the plant or plant cell can be altered.

In a cassette, the termination region may be native with the transcriptional initiation region, may be native with the operably linked nucleotide sequence of interest, may be native with the plant host, or may be derived from another source (i.e., foreign or heterologous to the promoter, the nucleotide sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262: 141-144; Proudfoot (1991) *Cell* 64: 671-674; Sanfacon et al. (1991) *Genes Dev.* 5: 141-149; Mogen et al. (1990) *Plant Cell* 2: 1261-1272; Munroe et al. (1990) *Gene* 91: 151-158; Ballas et al. (1989) *Nucleic Acids Res.* 17: 7891-7903; and Joshi et al. (1987) *Nucleic Acid Res.* 15: 9627-9639.

Where appropriate, the polynucleotides may be optimized for increased expression in the transformed plant. That is, the genes can be synthesized using plant-preferred codons for improved expression. See, for example, Campbell and Gowri (1990) *Plant Physiol.* 92: 1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17: 477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell, and the sequence may be modified to avoid predicted hairpin secondary mRNA structures.

The cassettes may additionally contain 5' leader sequences in the cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86: 6126-6130); potyvirus leaders, for example, TEV leader (Tobacco Etch Virus) (Gallie et al. (1995) *Gene* 165(2): 233-238), MDMV leader (Maize Dwarf Mosaic Virus) (*Virology* 154: 9-20), and human immunoglobulin heavy-chain binding protein (BiP) (Macejak et al. (1991) *Nature* 353: 90-94); untranslated leader from the coat protein mRNA of alfalfa mosaic virus (AMV RNA 4) (Jobling et al. (1987) *Nature* 325: 622-625); tobacco mosaic virus leader (TMV) (Gallie et al. (1989) in *Molecular Biology of RNA*, ed. Cech (Liss, N.Y.), pp. 237-256); and maize chlorotic mottle virus leader (MCMV) (Lommel et al. (1991) *Virology* 81: 382-385). See also, Della- Cioppa et al. (1987) *Plant Physiol.* 84: 965-968. Other methods known to enhance translation can also be utilized, for example, introns, and the like.

The cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85: 610-9 and Fetter et al. (2004) *Plant Cell* 16: 215-28), cyan florescent protein (CYP) (Bolte et al. (2004) *J. Cell Science* 117: 943-54 and Kato et al. (2002) *Plant Physiol* 129: 913-42), and yellow florescent protein (PhiYFP™ from Evrogen; see Bolte et al. (2004) *J. Cell Science* 117: 943-54). See generally, Yarranton (1992) *Curr. Opin. Biotech.* 3: 506-511; Christopherson et al. (1992) *Proc. Natl. Acad. Sci. USA* 89: 6314-6318; Yao et al. (1992) *Cell* 71: 63-72; Reznikoff (1992) *Mol. Microbiol.* 6: 2419-2422; Barkley et al. (1980) in *The Operon*, pp. 177-220; Hu et al. (1987) *Cell* 48: 555-566; Brown et al. (1987) *Cell* 49: 603-612; Figge et al. (1988) *Cell* 52: 713-722; Deuschle et al. (1989) *Proc. Natl. Acad. Aci. USA* 86: 5400-5404; Fuerst et al. (1989) *Proc. Natl. Acad. Sci. USA* 86: 2549-2553; Deuschle et al. (1990) *Science* 248: 480483; Gossen (1993) Ph.D. Thesis, University of Heidelberg; Reines et al. (1993) *Proc. Natl. Acad. Sci. USA* 90: 1917-1921; Labow et al. (1990) *Mol. Cell. Biol.* 10: 3343-3356; Zambretti et al. (1992) *Proc. Natl. Acad. Sci. USA* 89: 3952-3956; Baim et al., (1991) *Proc. Natl. Acad. Sci. USA* 88: 5072-5076; Wyborski et al. (1991) *Nucleic Acids Res.* 19: 4647-4653; Hillenand-Wissman (1989) *Topics Mol. Struc. Biol.* 10: 143-162; Degenkolb et al. (1991) *Antimicrob. Agents Chemother.* 35: 1591-1595; Kleinschnidt et al. (1988) *Biochemistry* 27: 1094-1104; Bonin (1993) Ph.D. Thesis, University of Heidelberg; Gossen et al. (1992) *Proc. Natl. Acad. Sci. USA* 89: 5547-5551; Oliva et al. (1992) *Antimicrob. Agents Chemother.* 36: 913-919; Hlavka et al. (1985) *Handbook of Experimental Pharmacology*, Vol. 78 (Springer-Verlag, Berlin); Gill et al. (1988) *Nature* 334: 721-724. Such disclosures are herein incorporated by reference.

The above list of selectable marker genes is not meant to be limiting. Any suitable selectable marker gene can be used in the present invention, and one of skill in the art will be able to determine which selectable marker gene is suitable for a particular application.

In preparing the cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810-812); rice actin (McElroy et al. (1990) *Plant Cell* 2: 163-171); ubiquitin (Christensen et al. (1989) *Plant Mol. Biol.* 12: 619-632 and Christensen et al. (1992) *Plant Mol. Biol.* 18: 675-689); pEMU (Last et al. (1991) *Theor. Appl. Genet.* 81: 581-588); MAS (Velten et al. (1984) *EMBO J.* 3: 2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Chemical-regulated promoters can be used to modulate the transcription and/or expression of a particular nucleotide sequence in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88: 10421-10425 and McNellis et al. (1998) *Plant J.* 14(2): 247-257) and tetracycline-inducible and tetracycline-repressible promoters (see, for example, Gatz et al. (1991) *Mol. Gen. Genet.* 227: 229-237, and U.S. Pat. Nos. 5,814,618 and 5,789,156), herein incorporated by reference.

Tissue-preferred promoters can be utilized to target enhanced transcription and/or expression within a particular plant tissue. Tissue-preferred promoters include those described in Yamamoto et al. (1997) *Plant J.* 12(2): 255-265; Kawamata et al. (1997) *Plant Cell Physiol.* 38(7): 792-803; Hansen et al. (1997) *Mol. Gen Genet.* 254(3):337-343; Russell et al. (1997) *Transgenic Res.* 6(2): 157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20: 181-196; Orozco et al. (1993) *Plant Mol. Biol.* 23(6): 1129-1138; Matsuoka et al. (1993) *Proc Natl. Acad. Sci. USA* 90(20): 9586-9590; and Guevara-Garcia et al. (1993) *Plant J* 4(3): 495-505. Such promoters can be modified, if necessary, for weak expression.

Leaf-preferred promoters are known in the art. See, for example, Yamamoto et al. (1997) *Plant J.* 12(2): 255-265; Kwon et al. (1994) *Plant Physiol.* 105: 357-67; Yamamoto et al. (1994) *Plant Cell Physiol.* 35(5): 773-778; Gotor et al. (1993) *Plant J.* 3: 509-18; Orozco et al. (1993) *Plant Mol. Biol.* 23(6): 1129-1138; and Matsuoka et al. (1993) *Proc. Natl. Acad. Sci. USA* 90(20): 9586-9590.

Root-preferred promoters are known and can be selected from the many available from the literature or isolated de novo from various compatible species. See, for example, Hire et al. (1992) *Plant Mol. Biol.* 20(2): 207-218 (soybean root-specific glutamine synthetase gene); Keller and Baumgartner (1991) *Plant Cell* 3(10): 1051-1061 (root-specific control element in the GRP 1.8 gene of French bean); Sanger et al. (1990) *Plant Mol. Biol.* 14(3): 433-443 (root-specific promoter of the mannopine synthase (MAS) gene of *Agrobacterium tumefaciens*); and Miao et al. (1991) *Plant Cell* 3(1): 11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed roIC and roID root-inducing genes of *Agrobacterium rhizogenes* (see *Plant Science* (Limerick) 79(1): 69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al., (1995) *Plant Mol. Biol.* 29(4): 759-772); and roIB promoter (Capana et al. (1994) *Plant Mol. Biol.* 25(4): 681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10: 108, herein incorporated by reference. Such seed-preferred promoters include, but are not limited to, Cim1 (cytokinin-induced message); cZ19B1 (maize 19 kDa zein); and milps (myo-inositol-1-phosphate synthase); (see WO 00/11177 and U.S. Pat. No. 6,225,529, herein incorporated by reference). Gamma-zein is a preferred endosperm-specific promoter. Glb-1 and oleosin are preferred embryo-specific promoters. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Where low level transcription or expression is desired, weak promoters will be used. Generally, by "weak promoter" is intended a promoter that drives transcription and/or expression of a coding sequence at a low level. By low level is intended at levels of about $1/1000$ transcripts to about $1/100,000$ transcripts to about $1/500,000$ transcripts. Alternatively, it is recognized that weak promoters also encompasses promoters that are expressed in only a few cells and not in others to give a total low level of transcription and/or expression. Where a promoter is expressed at unacceptably high levels, portions of the promoter sequence can be deleted or modified to decrease transcription and/or expression levels.

Such weak constitutive promoters include, for example, the core promoter of the Rsyn7 promoter (WO 99/43838 and U.S. Pat. No. 6,072,050), the core $^{35}$S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

In one embodiment, the polynucleotides of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9: 104-126; Clark et al. (1989) *J. Biol. Chem.* 264: 17544-17550; Della-Cioppa et al. (1987) *Plant Physiol.* 84: 965-968; Romer et al. (1993) *Biochem. Biophys. Res. Commun.* 196: 1414-1421; and Shah et al. (1986) *Science* 233: 478-481.

Chloroplast targeting sequences are known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5): 3335-3342); 5-(enolpyruvyl)shikimate-3-phosphate synthase (EPSPS) (Archer et al. (1990) *J. Bioenerg. Biomemb.* 22(6): 789-810); tryptophan synthase (Zhao et al. (1995) *J. Biol. Chem.* 270(11): 6081-6087); plastocyanin (Lawrence et al. (1997) *J. Biol. Chem.* 272(33): 20357-20363); chorismate synthase (Schmidt et al. (1993) *J. Biol. Chem.* 268(36): 27447-27457); and the light harvesting chlorophyll a/b binding protein (LHBP) (Lamppa et al. (1988) *J. Biol. Chem.* 263: 14996-14999). See also Von Heijne et al. (1991) *Plant Mol. Biol. Rep.* 9: 104-126; Clark et al. (1989) *J. Biol. Chem.* 264: 17544-17550; Della-Cioppa et al. (1987) *Plant Physiol.* 84: 965-968; Romer et al. (1993) *Biochem. Biophys. Res. Commun.* 196: 1414-1421; and Shah et al. (1986) *Science* 233: 478-481.

Methods for transformation of chloroplasts are known in the art. See, for example, Svab et al. (1990) *Proc. Natl. Acad. Sci. USA* 87: 8526-8530; Svab and Maliga (1993) *Proc. Natl. Acad. Sci. USA* 90: 913-917; Svab and Maliga (1993) *EMBO J.* 12: 601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Nat. Acad. Sci. USA* 91: 7301-7305.

The polynucleotides of interest to be targeted to the chloroplast may be optimized for expression in the chloroplast to account for differences in codon usage between the plant nucleus and this organelle. In this manner, the polynucleotides of interest may be synthesized using chloroplast-preferred codons. See, for example, U.S. Pat. No. 5,380,831, herein incorporated by reference.

In specific embodiments, the HDGL2 sequences of the invention can be provided to a plant using a variety of transient transformation methods. Such transient transformation methods include, but are not limited to, the introduction of the HDGL2 protein or variants and fragments thereof directly into the plant or the introduction of an HDGL2 transcript into the plant. Such methods include, for example, microinjection or particle bombardment. See, for example, Crossway et al. (1986) *Mol Gen. Genet.* 202: 179-185; Nomura et al. (1986) *Plant Sci.* 44: 53-58; Hepler et al. (1994) *Proc. Natl. Acad. Sci.* 91: 2176-2180 and Hush et al. (1994) *The Journal of Cell Science* 107: 775-784, all of which are herein incorporated by reference. Alternatively, the HDGL2 polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylimine (PEI; Sigma #P3143).

In certain embodiments the nucleic acid sequences of the present invention can be "stacked" with any combination of nucleic acids of interest in order to create plants with a desired phenotype. By "stacked" or "stacking" is intended that a plant of interest contains one or more nucleic acids comprising multiple nucleotide sequences so that the transcription and/or expression of multiple genes are altered in the plant. For example, the HDGL2 polynucleotide of the present invention can be stacked with any other polynucleotide(s) to produce plants having a variety of desired trait combinations including, for example, traits desirable for balanced amino acids (e.g., hordothionins; see U.S. Pat. Nos. 5,990,389; 5,885,801; 5,885,802; and 5,703,409, each of which is incorporated herein by reference); barley high lysine (Williamson et al. (1987) Eur. J. Biochem. 165: 99-106 and WO 98/20122); high methionine proteins (Pedersen et al. (1986) J. Biol. Chem. 261: 6279; Kirihara et al. (1988) Gene 71: 359; and Musumura et al. (1989) Plant Mol. Biol. 12: 123); increased digestibility (e.g., modified storage proteins) and thioredoxins (U.S. Ser. No. 10/005,429, filed Dec. 3, 2001).

An HDGL2 polynucleotide also can be stacked with one or more polynucleotides encoding a desirable trait such as a polynucleotide that confers, for example, insect, disease or herbicide resistance (e.g., Bacillus thuringiensis toxic proteins; U.S. Pat. Nos. 5,366,892; 5,747,450; 5,737,514; 5,723,756; 5,593,881; Geiser et al. (1986) Gene 48: 109); lectins (Van Damme et al. (1994) Plant Mol. Biol. 24: 825); fumonisin detoxification genes (U.S. Pat. No. 5,792,931); avirulence and disease resistance genes (Jones et al. (1994) Science 266: 789; Martin et al. (1993) Science 262: 1432; Mindrinos et al. (1994) Cell 78: 1089); acetolactate synthase mutants that lead to herbicide resistance such as the S4 and/or Hra mutations; inhibitors of glutamine synthase such as phosphinothricin or basta (e.g., the bar gene); and glyphosate resistance (EPSPS gene). Additional polynucleotides that can be stacked with an HDGL2 polynucleotide include, for example, those encoding traits desirable for processing or process products such as modified oils (e.g., fatty acid desaturase genes (U.S. Pat. No. 5,952,544; WO 94/11516); modified starches (e.g., ADPG pyrophosphorylases, starch synthases, starch branching enzymes, and starch debranching enzymes); and polymers or bioplastics (e.g., U.S. Pat. No. 5,602,321). An HDGL2 polynucleotide of the invention also can be stacked with one or more polynucleotides that provide desirable agronomic traits such as male sterility (e.g., U.S. Pat. No. 5,583,210), stalk strength, flowering time, or transformation technology traits such as cell cycle regulation or gene targeting (e.g., WO 99/61619; WO 00/17364; WO 99/25821).

These stacked combinations can be created by any method including but not limited to cross breeding plants by any conventional or TopCross methodology, (see for example 5,706,603) or genetic transformation. In this regard, it is understood that transformed plants of the invention include a plant that contains a sequence of the invention that was introduced into that plant via breeding. If traits are stacked by genetically transforming the plants, the nucleic acids of interest can be combined at any time and in any order. Similarly, where a method requires more than one step to be performed, it is understood that steps may be performed in any order that accomplishes the desired end result. For example, a transgenic plant comprising one or more desired traits can be used as the target to introduce further traits by subsequent transformation. The traits can be introduced simultaneously in a co-transformation protocol with the polynucleotides of interest provided by any combination of cassettes suitable for transformation. For example, if two sequences will be introduced, the two sequences can be contained in separate cassettes (trans) or contained on the same transformation cassette (cis). Transcription and/or expression of the sequences can be driven by the same promoter or by different promoters. In certain cases, it may be desirable to introduce a cassette that will suppress the expression of the polynucleotide of interest. This may be combined with any combination of other cassettes to generate the desired combination of traits in the plant. Alternatively, traits may be stacked by transforming different plants to obtain those traits; the transformed plants may then be crossed together and progeny may be selected which contains all of the desired traits.

It is understood that in some embodiments the nucleic acids to be stacked with HDGL2 can also be designed to reduce or eliminate the expression of a particular protein, as described in detail herein for HDGL2. Thus, the methods described herein with regard to the reduction or elimination of expression of HDGL2 are equally applicable to other nucleic acids and nucleotide sequences of interest.

Transformation protocols as well as protocols for introducing polypeptides or polynucleotides into plants may vary depending on the type of plant or plant cell, i.e., monocot or dicot, targeted for transformation. Suitable methods of introducing polypeptides or polynucleotides into plant cells and subsequent insertion into the plant genome include microinjection (Crossway et al. (1986) Biotechniques 4: 320-334), electroporation (Riggs et al. (1986) Proc. Natl. Acad. Sci. USA 83: 5602-5606, Agrobacterium-mediated transformation (U.S. Pat. No. 5,563,055; U.S. Pat. No. 5,981,840), direct gene transfer (Paszkowski et al. (1984) EMBO J. 3: 2717-2722), and ballistic particle acceleration (see, for example, U.S. Pat. No. 4,945,050; U.S. Pat. No. 5,879,918; U.S. Pat. No. 5,886,244; U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); McCabe et al. (1988) Biotechnology 6: 923-926); and Lec1 transformation (WO 00/28058). Also see Weissinger et al. (1988) Ann. Rev. Genet. 22: 421-477; Sanford et al. (1987) Particulate Science and Technology 5: 27-37 (onion); Christou et al. (1988) Plant Physiol. 87: 671-674 (soybean); McCabe et al. (1988) Bio/Technology 6: 923-926 (soybean); Finer and McMullen (1991) In Vitro Cell Dev. Biol. 27P: 175-182 (soybean); Singh et al. (1998) Theor. Appl. Genet. 96: 319-324 (soybean); Datta et al. (1990) Biotechnology 8: 736-740 (rice); Klein et al. (1988) Proc. Natl. Acad. Sci. USA 85: 4305-4309 (maize); Klein et al. (1988) Biotechnology 6: 559-563 (maize); U.S. Pat. No. 5,240,855; U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91: 440-444 (maize); Fromm et al. (1990) Biotechnology 8: 833-839 (maize); Hooykaas-Van Slogteren et al. (1984) Nature (London) 311: 763-764; Bowen et al., U.S. Pat. No. 5,736, 369 (cereals); Bytebier et al. (1987) Proc. Natl. Acad. Sci. USA 84: 5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) Plant Cell Reports 9: 415-418 and Kaeppler et al. (1992) Theor. Appl. Genet. 84: 560-566 (whisker-mediated transformation); D'Halluin et al. (1992) Plant Cell 4: 1495-1505 (electroporation); Li et al. (1993) Plant Cell Reports 12:

250-255 and Christou and Ford (1995) *Annals of Botany* 75: 407-413 (rice); Osjoda et al. (1996) *Nature Biotechnology* 14: 745-750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5: 81-84. These plants may then be grown and either pollinated with the same transformed strain or different strains; the resulting progeny having the desired phenotypic characteristic can then be identified. Two or more generations may be grown to ensure that the desired phenotypic characteristic is stably maintained and inherited and then seeds harvested to ensure that stable transformants exhibiting the desired phenotypic characteristic have been achieved. In this manner, the present invention provides transformed seed (also referred to as "transgenic seed") having a nucleotide construct of the invention, for example, a cassette of the invention, stably incorporated into their genome.

As used herein, the term "plant" includes plant cells, plant protoplasts, plant cell tissue cultures from which maize plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. The term "seed" is used to include seeds (e.g., flax seeds) and kernels (e.g., maize kernels), which can accumulate oil. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* spp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art, including, but not limited to, stable transformation methods, transient transformation methods, and virus-mediated methods.

Further, the term "introducing" is intended to encompass methods of presenting to the plant the polynucleotide or polypeptide through traditional breeding methods, where one plant with the desired trait is cross-pollinated with another plant lacking the trait. Backcrossing methods may be used to introduce the gene into the plants. This technique has been used for decades to introduce traits into a plant. An example of a description of this and other plant breeding methodologies that are well known can be found in references such as "Plant Breeding Methodology" edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

Pedigree breeding starts with the crossing of two genotypes, such as a transformed (i.e. transgenic) inbred line and one other elite inbred line having one or more desirable characteristics that is lacking or which complements the first transgenic inbred line. Alternatively, the inbred line can be the result of a mutation of the gene of interest, such as those which can be artificially induced by the plant breeder. If the two original parents do not provide all the desired characteristics, other sources can be included in the breeding population. In the pedigree methods, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→F5, etc. After a sufficient amount of inbreeding, successive filial generations will serve to increase seed of the developed inbred. Preferably, the inbred line comprises homozygous alleles at about 95% or more of its loci. It may be desirable to breed a plant having a HDGL2 encoding gene that is in the homozygous condition, that is, where each allele or alternative form of the genetic locus is identical.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Thus, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

In other embodiments, the polynucleotides of the invention may be introduced into plants by contacting plants with a virus or viral nucleic acids. Generally, such methods involve incorporating a nucleotide construct of the invention within a viral DNA or RNA molecule. It is recognized that an HDGL2 of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191; 5,889,190; 5,866,785; 5,589,367; 5,316,931, and Porta et al. (1996) *Molecular Biotechnology* 5: 209-221; herein incorporated by reference.

The terms "increase", "decrease", "inhibit", and "reduce or eliminate" are used in a relative sense with respect to a pre-defined value. For purposes of the present invention, the pre-defined value is the level of HDGL2 gene expression in a corresponding plant or plant cell that has not been manipulated according to a method of the invention.

The terms "reduce or eliminate" are used together because, depending on a particular assay being used, it may not be possible to determine, for example, whether expression of an HDGL2 gene is reduced below a level of detection of a particular assay, or completely inhibited. Nevertheless, according to a method of the invention, where such HDGL2 gene expression is reduced or eliminated, increased seed oil content will be ascertainable using methods as disclosed herein or otherwise known in the art. By way of example, increased seed oil content of mutant p777 plants, which were obtained following treatment of *A. thaliana* Columbia plants with T-DNA, was identified by comparing the density of seeds produced by the mutant plants with seeds produced by the parental wild type plants (see Example 1).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

The following examples are set forth as illustrative in nature and are not intended to limit the scope of the invention.

EXAMPLE 1

Glabra2 Gene Expression is Associated with Seed Oil Accumulation

This example demonstrates that the high seed oil content in a mutant plant line is due to knockout of the *Arabidopsis* glabra2 gene.

Methods

Plant Material and Growth

*Arabidopsis thaliana* plants were grown in growth chamber at 25° C. day and 20° C. night with 16 hr of light and 8 hr of dark. Approximate 17,000 activation lines were obtained from *Arabidopsis* Biological Resource Center at Ohio (see, also, Weigel et al., *Plant Physiol.* 122(4):1003-1013, 2000, which is incorporated herein by reference). The activation-tagging vector used herein confers resistance the herbicide glufosinate (Basta) in transformed plants. The vector is a T-DNA vector containing four copies of an enhancer element from the constitutively actie promoter of the cauliflower mosaic virus (CaMV) 35S gene. These enhancers can cause transcriptional activiation of the nearby genes. Because the activated genes are associated with a T-DNA insertion, this approach has become known as activation-tagging. Weigel et al., "Activation tagging in *Arabidposis*" *Plant Physiol.* 2000 April; 122(4): 1003-13. The sequence used here is found at GenBank accession number AF187951, pSK1015.

Density Screening for High Oil Mutant

*Arabidopsis* seeds were separated according to their density. Density layers were prepared using mixtures of 1,6 dibromohexane (density, d=1.6), 1-bromohexane (d=1.17) and mineral oil (d=0.84) at different ratios. From the bottom to top of tube, 6 layers of organic solvents were added one-by-one. The ratios of 1,6 dibromohexane:1-bromohexane: mineral oil for each layer were 1:1:0, 1:2:0, 0:1:0, 0:5:1, 0:3:1, 0:0:1. The density of layers was adjusted such that about 99% of seed stayed in the middle layer, and only a few seeds went to the upper layers. About 5000 mutagenized seeds were loaded to the top of tube and centrifuged for 5 min at 5000 rpm such that the seeds separated according to their density. The seeds in the upper two layers (least dense) were collected as high oil candidates and propagated to obtain T2 seeds.

Seed Oil Measurement

Seed oil content was determined using a PCT-20/20B NMR analyzer (Process Control Technology; Fort Collins Colo.). Vegetable oil was used as standard. Approximately 20-80 mg seed per line was used for analysis. The amount of oil determined by NMR was consistent with the amount of oil as determined by hexane extraction.

Plasmid Rescue

Plasmid rescue was carried as described by Weigel et al. (supra, 2000). Genomic DNA was isolated from p777 leaves using the DNeaSy™ Plant Mini kit (Qiagen; Valencia Calif.), according to the manufacturer's instructions, digested with an appropriate restriction enzyme, and ligated overnight at 14° C. Ligated DNA was transformed into SURE 2 ultracompetent cells (Stratagene; La Jolla Calif.). Plasmids were isolated from transformants and sequenced.

Southern Blot and Northern Blot Analysis

DNA and RNA gel blot hybridization was performed according to standard procedures (Sambrook et al. (1989) "Molecular Cloning: A laboratory manual (Cold Spring Harbor Laboratory Press), which is incorporated herein by reference). RNA was isolated from siliques at 7, 10, and 14 days after pollination, as described by Schultz et al. (1994) *Plant Mol. Biol. Rept.* 12:310-316, which is incorporated herein by reference).

Results

High Oil Mutant Isolation

To identify key genes that control oil biosynthesis, a high throughput density screening method to isolate high seed oil mutant was developed. Screening was based on changes of seed density caused by oil content. Mutagenized seeds were loaded to a tube containing several layers of organic solvents with different densities. Following centrifugation, seeds were separated according to their density. Gradients were such that most of the seeds stayed in the middle layer, while a few seeds went to top, lower density layer of organic solvent or to bottom, higher density layer. Low density seeds were collected as potential high oil content candidates, and propagated to obtain homozygous $T_2$ seeds.

Oil content of bulk $T_2$ seed collected from candidate lines were determined by NMR. Most of candidate lines showed no increase in seed oil content in $T_2$, suggesting that either low density in $T_1$ was caused by non-oil factor, or high oil in T1 was due to an environmental factor. One line, designated p777, isolated from the activation population continued to show lower seed density and higher seed oil content compared to wild type. In three independent experiments, p777 exhibited oil content increases ranging from 3% to 5% on a mature seed dry weight basis. The fatty acid composition of p777 seed showed no difference from the wild type. P777 plants grew normally, and the leaf surface appeared glabrous and had no trichomes. Seeds collected from p777 were of normal size and weight as compared to wild type.

P777 has a T-DNA Insertion in the glabra2 Gene

To determine where T-DNA was inserted in p777 genome, T-DNA insertion in p777 was characterized in three ways. First, in p777 $F_2$ segregating population, the ratio of Basta (60 g l(-1) glufosinate) resistant plants to Basta sensitive plants was 3:1, indicating that there was a single T-DNA insertion in the P777 genome. Second, plant DNA adjacent to the T-DNA insertion was recovered by plasmid rescue. Sequence analysis of flanking DNA indicated that T-DNA was inserted into the glabra2 gene on chromosome 1. Third, Southern blot hybridization using the Basta gene as a probe detected two fragments with SpeI, EcoRI, and BamHI digestion, and one band with HindIII digestion. Based on the published genome sequence and T-DNA sequence, it was determined that two T-DNA molecules were inserted in the glabra2 gene. Sequencing of the insertion region confirmed that the second T-DNA was inserted 45 nucleotides from the first T-DNA insertion.

High Oil Phenotype in p777 is Due to Knockout of the glabra2 Gene

To determine whether high oil is caused by T-DNA insertion, p777 was crossed to wild type plant. Seed oil content of 64 $F_2$ plants were determined by NMR. Individual F2 plant genotype was determined in $F_3$ seedling based on Basta resistance and leaf trichome, wherein 1) Basta resistant plants without trichome indicates homozygous mutant plant; 2) Basta resistant plants with trichome are heterozygous; and 3) Basta sensitive plants with trichome are wild type plants.

Homozygous P777 plants had higher seed oil content than heterozygous plants and wild type plants. Heterozygous plants had the same amount of oil as the wild type plants, indicating that high oil is recessive. Co-segregation of seed oil and leaf trichome phenotype indicated that high seed oil was caused by T-DNA insertion.

High oil content in P777 seed could have been caused by knockout of glabra2 gene function or, because the T-DNA contained 4 copies of 35S enhancer, could have been caused by activation of a gene adjacent to the T-DNA. Five genes are adjacent to the T-DNA insertion site: gene A encoding a D-isomer specific 2-hydroxyacid dehydrogenase, gene B encoding a protein of unknown function, gene C encoding a 30S ribosomal protein S17, gene D encoding a protein of unknown function, and gene E encoding a putative sugar transporter.

Northern blot analysis and RT-PCR analysis indicated that only gene B expression was up-regulated in p777. To determine whether overexpression of gene B caused the high oil phenotype, a construct containing 4 copies of the $^{35}$S enhancer inserted before a gene B genomic fragment, and a construct containing the SLC1 constitutive promoter before the gene B coding sequence were prepared, and introduced into wild type plants. Transgenic plants containing the expression constructs showed no difference in seed oil content as compared to wild type plants. These results demonstrate that overexpression of gene B is not responsible for the high oil phenotype in P777.

In order to determine whether glabra2 gene knockout was responsible for the high oil phenotype, an EMS allele of the glabra2 mutant, gl2-1, was examined. The gl2-1 mutant showed higher seed oil content and lower seed density than the corresponding wild type Landsberg erecta. This result confirms that knockout of the glabra2 gene is responsible for the high oil phenotype in P777.

These results demonstrate that the reduction or inhibition of expression of an HDGL2 gene such as glabra2 results in increased seed oil levels in plant seed.

EXAMPLE 2

Increasing Oil Production in Corn by Decreasing Zmocl1 Gene Expression

HDGL2 gene expression is reduced or eliminated by expressing seed-specifically a hairpin RNA (hpRNA) in maize cells. For this purpose, the expression cassette is designed to carry a polynucleotide that expresses an RNA molecule that hybridizes with itself to form a hairpin structure that comprises a single-stranded loop region and a base-paired stem. The base-paired stem region comprises a sense sequence corresponding to a part of the endogenous messenger RNA encoding Zmocl1, and an antisense sequence that is fully or partially complementary to the sense sequence. The hpRNA molecules are highly efficient at inhibiting the expression of Zmocl1. A seed specific promoter such as oleosin promoter is operably linked to the polynucleotide. These and other elements of the invention are assembled into a vector ready for *Agrobacterium*-mediated transformation (see Example 3).

In one experiment, a 1443 bp fragment (ZM-OCL1 (TR1)) from near the 3' end of the coding sequence of ZM-OCL1 (Outer Cell Layer of the embryo, EST# ceb1.pk0048.d3) was ligated behind the promoter from the 16KD oleosin gene of *Z. mays* (OLE PRO). Similarly, a 410 bp fragment of the ZM-OCL1 coding sequence (near the 5' end of the above-described fragment) was isolated by polymerase chain reaction cloning and inserted at the end of the TR1 fragment, in an inverted orientation relative to TR1. This expression cassette was then inserted into a binary vector containing a UBI PRO: UBI INTRON1:MOPAT:PINII TERM selectable marker and flanked by Right border (RB) and left border (LB) sequences. This plasmid, designated PHP20568, was introduced into *Agrobacterium* for subsequent transformation of *Z. mays*.

Transgenic events are recovered and advanced to the greenhouse. The resulting plants are either self pollinated or outcrossed to a suitable genetic background for monitoring oil content changes. At maturity, ears are collected from the plants and a portion of the seed yield (typically 20 kernels from each year) is dissected to separate the embryo from the endosperm. The dissected embryos are lyophilized and the oil content in each embryo is determined using a PCT-20/20B NMR analyzer. Oil content changes are measured by changes in total embryo oil and percentage embryo oil by lyophilized weight. High oil candidates are identified when the oil content changes correlate with co-segregation analysis of the transgene using PCR.

EXAMPLE 3

Production of Transgenic Maize Plants Via
*Agrobacterium*-Mediated

For *Agrobacterium*-mediated transformation of maize with a vector designed to reduce or inhibit the expression of Zmocl1, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the nucleotide sequences of the invention to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 4

Screening Of Zmocl1 Tusc Mutants

This example describes a procedure to identify plants containing Mu inserted into Zmocl1, identified as SEQ ID No. 3 herein. The Trait Utility System for Corn (TUSC) is a method that employs genetic and molecular techniques to facilitate the study of gene function in maize. Studying gene function implies that the gene's sequence is already known, thus the method works in reverse: from sequence to phenotype. This kind of application is referred to as "reverse genetics", which contrasts with "forward" methods that are designed to identify and isolate the gene(s) responsible for a particular trait (phenotype). Pioneer Hi-Bred International, Inc., has a proprietary collection of maize genomic DNA from approximately 42,000 individual $F_1$ plants (Meeley and Briggs (1995) *Maize Genet. Coop. Newslett.* 69:67-82). The genome of each of these individuals contains multiple copies of the transposable element family, Mutator (Mu). The Mu family is highly mutagenic; in the presence of the active element Mu-DR, these elements transpose throughout the genome, inserting into genic regions, and often disrupting gene function. By collecting genomic DNA from a large number (42,000) of individuals, Pioneer has assembled a library of the mutagenized maize genome.

Mu insertion events are predominantly heterozygous; given the recessive nature of most insertional mutations, the $F_1$ plants appear wild-type. Each of the $F_1$ plants is selfed to produce $F_2$ seed, which is collected. In generating the $F_2$ progeny, insertional mutations segregate in a Mendelian fashion so are useful for investigating a mutant allele's effect on the phenotype. The TUSC system has been successfully used by a number of laboratories to identify or confirm the function of a variety of genes (Bensen et al. (1995) *Plant Cell* 7:75-84; Mena et al. (1996) *Science* 274:1537-1540; Frey et al. (1997) *Science* 277:696-699; Chuck et al. (1998) *Genes & Development* 12:1145-1154; Roy and Barkan (1998) *J. Cell Biol.* 141:1-11).

Briefly, mutant alleles of Zmocl1 caused by Mu insertion is identified by PCR screening using Zmocl1 sequence specific primers. To alleviate problems of expressivity, an introgression series will be initiated with the introduction of each Mu-disrupted allele into a number of well-characterized inbred lines (W23, B73 and Mol7). At each generation, heterozygous mutants will also be self-fertilized to generate homozygous mutants, which can be analyzed in the following studies. All Mu-disrupted alleles isolated will be crossed to generate pertinent double mutants. Mutant plants under analysis will always be compared to control siblings, segregating as a result of this cross, carrying wild type Zmocl1 loci in the same genetic background.

EXAMPLE 5

Oil Content of Zmocl1 Tusc Mutant

A Mu insertional maize line was identified from Pioneer TUSC collections. In this line, a Mu element was inserted into Zmocl1 coding region. Homozygous mutant seeds were obtained and the embryo was dissected. Oil concentration of the embryo was determined by NMR. Knockout of Zmcol1 gene led to an increase in embryo oil concentration. Average Zmcol1 mutant embryo oil concentration is 31.4% while the average embryo oil concentration of null is 25.2%.

EXAMPLE 6

Production of Transgenic *Arabidopsis* Plants Via *Agrobacterium* Mediated Transformation HDGL2 gene expression is reduced or eliminated by expressing seed-specifically a hairpin RNA (hpRNA) in *Arabidopsis* cells, using the procedures as outlined in Example 2. As described, the expression cassette is designed to carry a polynucleotide that expresses an RNA molecule that hybridizes with itself to form a hairpin structure that comprises a single-stranded loop region and a base-paired stem. The base-paired stem region comprises a sense sequence corresponding to a part of the endogenous messenger RNA encoding Zmocl1, and an antisense sequence that is fully or partially complementary to the sense sequence. For *Agrobacterium* mediated transformation of *Arabidopsis* with the vector designed to reduce or inhibit the expression of the glabra2 gene, a simple method is employed. Clough, S J, Bent, A F "Floral dip: a simplified method for *Agrobacterium*-mediated transformation of *Arabidposis thaliana* " *Plant J.* 1988 December; 16(6): 735-43). Briefly, flowering *Arabdiposis* plants are dipped in to the *Agrobacterium* culture carrying the designed vector. Seeds are collected from *Agrobacterium* dipped plants and germinated on soil. Because the Bar resistance gene is present in the T-DNA, transformed plants are selected based on their resistance to the herbicide Basta. Homozygous $T_2$ seeds can be obtained by selfing $T_1$ plants. Seed oil content of $T_2$ seeds can be determined by NMR.

Although the invention has been described with reference to the above examples, it will be understood that modifications and variations are encompassed within the spirit and scope of the invention.

What is claimed is:

1. A method of increasing seed oil content in a plant, the method comprising introducing into the plant a nucleic acid molecule which reduces or eliminates the expression of a nucleotide sequence comprising SEQ ID NO: 1 where the reduction or elimination of expression of said sequence results in increased seed oil content, such that seed oil content in the plant is increased when compared to a plant not having the nucleic acid molecule and selecting a plant having said increased seed oil content.

2. The method of claim 1 wherein the nucleic acid molecule introduced comprises a complementary nucleotide sequence of SEQ ID NO: 1.

3. The method of claim 1 wherein the nucleic acid molecule causes co-suppression of SEQ ID NO: 1.

4. The method of claim 1 wherein the nucleic acid molecule comprises a hairpin structure RNA molecule.

5. The method of claim 1 wherein the nucleic acid molecule interferes with expression of SEQ ID NO: 1.

6. A method of increasing seed oil content in a plant, the method comprising reducing or eliminating expression of a nucleotide sequence comprising SEQ ID NO: 1, where the reduction or elimination of expression of said sequence results in increased seed oil content, such that seed oil content in the plant is increased compared to a plant not having such reduced or eliminated expression, and selecting a plant having said increased seed oil content.

7. The method of claim 6 comprising mutating SEQ ID NO: 1.

8. The method of claim 1, wherein the nucleic acid molecule is a variant of SEQ ID NO: 1, such that expression of SEQ ID NO: 1 in the plant is reduced or eliminated.

9. The method of claim 8 wherein the nucleic acid molecule is a truncated variant of SEQ ID NO: 1.

10. A method of increasing seed oil content in a plant, the method comprising the steps of:

(a) transforming a plant cell with at least one expression cassette that expresses a polynucleotide that reduces or eliminates the expression of a polynucleotide sequence comprising SEQ ID NO: 1;
(b) regenerating a transformed plant from the transformed plant cell of step (a); and
(c) recovering transformed seed from the transformed plant, wherein the seed is characterized by increased oil content as compared to a wild type seed.

* * * * *

SEQUENCE LISTING

```
<160> NUMBER OF SEQ ID NOS: 10

<210> SEQ ID NO 1
<211> LENGTH: 7715
<212> TYPE: DNA
<213> ORGANISM: Arabidopsis thaliana
<220> FEATURE:
<221> NAME/KEY: gene
<222> LOCATION: (0)...(0)
<223> OTHER INFORMATION: genomic DNA

<400> SEQUENCE: 1
gatatgatat cagatctggg aatcctccca gagaaacttt gccactgaac caagccatct      60
ctacttgaga gatatatctg gaaactcgat cgacttaaat ctcagaaatc accggaccag     120
atccatctcc agccctgtgg cttccaagga aaacaatcaa ccaatcgagt ttagatccca     180
attacatcac tgaatcaatt attaagacga ggcgattgga taaagcagaa tagagctatc     240
tattgggatc atcaatggct tacgagaagg agatgcgtcg tccttgccgt cgtgatcgaa     300
ttccggagga gagagaccca cccctatgtg ttttatgttt ttttagatcc aacaaaatcc     360
aaatcctttt ttttccctcg gccaccggcg gtacaaacgg cgtcgtttcg cggattagaa     420
aaacgttctg tcttgatatc atttacttca ttctaagcgg ctttggtctg aatttttttat     480 atacaaggcc tgtctccgtt tttgtaaagg gaaaacagta ggatccattt tagcctctgt     540
aagtaacaat attgggcccc taaaagccca cccattttgg ggccagcaaa ccaaggcacc     600
ctcggttccg cacgctcgct aagacgctaa cctatgcata tgttgatatg ttttttctct     660 tcctttggt atgaatcttg atttgttttg atactcatga tgtacattcg tattctctta     720
cgtattgtaa accatcctat ttcagatcac gattatatct ttacgtttac attttttcatt     780 tttatttctg tttgaatgtt acaatttact agtagagtta ttcattaaaa tactacaact     840
ggtatacaga aatgtaattt gagtgataaa ttatatgaaa taattaagta atatatgtga     900
tatttatgga tccaaacaaa aactaattac tggttcattt tctattttag atgtaagcaa     960
aatgtgtaag attcaaggta tatatatatc ccaatatacg tatatatgtg gtactcacta    1020
gctagtagct ctctcacaac tgtgtctttt ggttttcatc agctgatcct ctccaactaa    1080
ctatccatct tttgtttgc ggttggactt ggaggtacca agaatattag caacgtacga    1140
```

```
ctcgtatggt atcatttcct ttgtacaaaa agtgaatatc aaaatgcatt gtattaatta    1200
tatataagtt agtatatgga gttagttgtc ctcactgtct ttatctggcg caatctccta    1260
tgccaccatt ccctcttcac acgtacgtgt gcacactcga tgtcacattt gtataaacac    1320
gtttgctttt agcgtgagat catcaccata ttccattttt ggtgggtcag ttctctttct    1380
agatagttat ttgtaaggac gtgaattaaa agggatcgtc gtcacttgtt gagataaaag    1440
aaaagatata tggtcagttt ctgcatcttg gaatcaactt aagggttgtc ttaattaatt    1500
ttgatagacc ctactttaaa aattaattag ttgctttcat tggccctcaa taagaaaagc    1560
caaaaaagaa agaagactgg tcttggaagt ttgccaacac gggtaataga ttaatggtga    1620
aaagggcgaa tttttttacc caaaccccta attaagtaga agtattaatc gagagcaaaa    1680
gagagagaga gagtcagtag ccaaaaggaa tgaatggaag aaagaaaaag gaatctctat    1740
aggcagcata tattcaagta attaattaaa gtagatagat agagcaaaag gagaggttag    1800
gaggcattaa ttaattattt aagagcatgt ggtgaatgta aatgtttatg gttgcttccc    1860
tctctataca ttatgtatct acctttccta actaacactt ccctaggccg tacgacgact    1920
aacaaagaaa aaaacaaaag aaactgataa agcttttgaa ttgtagataa atcatctgct    1980
acagttatac cattatatat cttattaaag acctaagttt ccttcactat acgtcttcgt    2040
ccatttacgt acgtattata cggacggttt aagctactat atctatattg ttaacaatgt    2100
aactgttgag atatatcttg caataatatg tcatggtgta tgcatacgat aatatgaatc    2160
aatgtttgaa atcttgacgt gcccgtgata caataagatg atcaaaattt caaatttgt     2220 caaatattaa aacaacatac acatacacat gtgtccaggt ggcattataa aatgtatata    2280
tggtggatat agagagagag ggagatgcgt atagtgaata ggaaagtaag taataaagag    2340
agggtggagg aattggaaag gggttggagg caaacccata aagagcattc atttccttt     2400 aaggtcgctg aaattaatga gtaacgatcg gtcaatgcct ctcgctgacc ttttctttt     2460 tttacaacaa caaataaaaa taaaataaat ttcgacgtct ctttccgctg ctgaattaca    2520
tttgttgaat taattttctc tgcttacgta cgtcttctaa actttctcta tccgaattct    2580
tttttaactt tctaacttat attcaacaac tcttcttttcc tgcctttacc gttagtctaa    2640
ttgttttcct aatactgcta cgtacatacc cctactatac tagtcagtgt attagattcg    2700
attgggatta atccaggaat atagatatcc cattagtttt tataaaaata ttggaagagg    2760
acaagtctca agcaatttag ggttccatgt agcgctgcaa tatactgtta gtaactctct    2820
cttacccata tattgtatat gctaattctt atcaaatata tatatatgct ctcccagag    2880 tcccagtttc ctataatcct gacgcaatta tactaataga gccaagttta cataataaag    2940
tatatatgat taatagatag ggtttcttat taagccatat cttaaattaa gatgtgatga    3000
tagcgttttg tataagttac caattgtttg aaagaagaga tcatcacaat aataaatcat    3060
aagtagtagt atatagtaat aaataaatac acaagtcata ataagagtaa tgagaggata    3120
attaaggagg gaagaagaaa gcagaaaatg cggttggaga attaggtgct aaaagttagt    3180
tgagtccatc tcagtatcta acggtcaact ctctctctct ctagagaaaa caattaagaa    3240
atctgacata cacatatgtc tctctctctc tctctctcta gtctatacac acaattcaat    3300
taaagaagag acagagaagt tcgtcttttt tgtttttata cccttaaatc aatcatgcaa    3360
ttgtaaccct tccttcttat tctcattcct tccccccctg tctacagtaa tctatagcaa    3420
cgccattatg tactactttt aacggataat ttgctcatgt ttcaatatgg cttcattgta    3480
tatatgttca agttcttctc aatccttttat atcattccaa cataattcat attaaagtta    3540
```

```
gtagctgaaa ttggaaggct gatatatttt ccataattca aatttgaatt ttgctcatca      3600
tatatatatg tatatattaa aaatcgaata ttaagaagaa aaatgaagtc gatcgatggc      3660
tgccaatgct gtagctggcc atgttttaaa ctactcaatt gtcggattga agtatagcca      3720
aaatatataa aaccgtaaaa ggactaaata taataatata ataggtatta attaattaaa      3780
actaattaat tataaaagaa gcacctaaaa gtcaagagca gtagagaaat ggaagaaata      3840
tctgaaaaac gaccgcttat atatatatgt atcattggaa ttgtagaggc tatatatata      3900
tatatatata tatatatata tatcgatctt agcttatata ttaattgaaa gtacattttg      3960
gtgtataagt aattaaagaa gaaagaaaaa aagagagata atatataagg aagaaggagt      4020
gcgaggagaa gagggaagag atcataatta agcaaagaag ctagctaggg acaggatttg      4080
tatgtcaatg gccgtcgaca tgtcttccaa acaacccacc aaagactttt tctcctctcc      4140
agccctctct ctatctctcg tatactactc tctcttttct acatacatgt acttgctagc      4200
tctcacataa acatatatta tatatatgtc ttgattttaa tggagatagg aatatataca      4260
ggctgggata ttccggaatg catcctccgg cagcaccaac cctgaggagg atttcctggg      4320
cagaagagta gttgacgatg aggatcgcac tgtggagatg agcagcgaga actcaggacc      4380
cacgagatcc agatcagagg aggatttgga gggtgaggat cacgacgatg aggaggagga      4440
agaggaggac ggcgcagctg gaaacaaggg cactaataag agaaagagga agaagtatca      4500
tcgtcacacc accgatcaga tcagacacat ggaagcgtac gttcgatata attattccat      4560
ccttacctag ctaactaatt aaaccccccca ccccactttt taataagtat aaacttaata      4620
attatgcttc acaaattaaa acacttaatt aggggattcc gattcattag ggctagcttc      4680
tatcaagaaa cattcattag ttgttttttc cggtgctcat atttcttgat gttttataag      4740
taattatgat tttaatccct ttcttcggta tatactgtag tacttaatta gtggaagaag      4800
gagaaggtgt cttgcgttga agagcaattc tcaattacgc accttcaatt ctccattaat      4860
ttcacataca tatatatact tagatgatgt attcatacaa atatattgcc gatcgatgat      4920
atatgatcca gcattagttt caatgcgctt atatggtttc ggacgcttac tcgttattat      4980
tccccgtctt ctcctgacat gactgtaggt acatgcgcgt tataacgtat ataaaggctt      5040
aaacaataaa gtgttaattt gtttcatcac aattaaagct gatcagtaat agtatacata      5100
tgcctagtta gggttcagtt gcatgtaaag attttcatct tttagaaatg tctgaatttg      5160
aggacgttgc aggctattca aagagacacc acatccggac gagaagcaaa gacagcagct      5220
gagcaagcaa ctagggctgg cccctcgcca ggtcaagttc tggttccaaa accgccgcac      5280
acagatcaag gtaatgtata tcttacgtga tatggatttt tgtctgacta tagtagtata      5340
tatatagttt atgaatcaat catgcatgga caggctattc aagaacggca cgagaactcc      5400
ctgctcaagg cggaactaga gaagctgcga gaggaaaaca aagccatgag ggagtctttt      5460
tccaaggcta attcctcctg ccccaactgc ggaggaggcc ccgatgatct ccacctcgaa      5520
aactccaaac tgaaagccga gctcgataag cttcgtgcag ctcttggacg cactccctat      5580
cccctgcagg cttcatgctc cgacgatcaa gaacaccgtc tcggctctct cgatttctac      5640
acgggcgtct ttgccctcga gaagtcccgt attgccgaga tttctaaccg agccaccctt      5700
gaactccaga agatggccac ctcaggcgaa cctatgtggc tccgcagcgt tgagactggc      5760
cgtgagattc tcaactacga tgagtacctc aaggagtttc cccaagcgca agcctcttcg      5820
tttcctggaa ggaaaaccat cgaagcatct agagatgcgg ggattgtgtt tatggacgca      5880
```

-continued

| | |
|---|---|
| cataaacttg cccagagttt catggacgtg gtacttttcc attatttatt actgttacca | 5940 |
| gctactataa cttattctat gtgtataaaa aggaattgat gtgtacgtgt aacgcgcagg | 6000 |
| gacaatggaa agagacattt gcatgcttga tctcaaaggc tgcaacggtc gatgttatcc | 6060 |
| ggcaaggcga agggccttca cggatcgacg gggctattca gctggtgagt actcatcaat | 6120 |
| atatacatat agtgataatt gatgaatgac gactcagctg atacatggga tggatatggt | 6180 |
| ttataactat tgtggcagat gttcggagag atgcagctgc tcactccggt cgtccccaca | 6240 |
| agagaagtgt acttcgtgag aagctgccgg cagctgagcc ctgagaaatg gcaatagtg | 6300 |
| gacgtctcgg tctccgtgga ggacagcaac acggagaagg aggcttctct tctgaaatgt | 6360 |
| cgaaaactcc cctccggttg catcatcgag gacacctcca acggtcactc caaggtcacc | 6420 |
| tgggtggagc acctcgacgt gtctgcatcc acagttcagc ctctcttccg ctccttagtc | 6480 |
| aacaccggtt tggcctttgg ggctcgacac tgggtcgcca cccttcagct ccattgcgaa | 6540 |
| cgccttgtct tcttcatggc taccaacgtc cccaccaaag actctctcgg tccgtctata | 6600 |
| tatccggatc ctccatttac actctctatc tttctttata tataaccttt tcactcctct | 6660 |
| gttgataatc aggagttaca actcttgccg ggagaaagag tgtgctgaag atggctcaga | 6720 |
| gaatgacaca aagcttctac cgcgccattg ctgcatcaag ctaccatcaa tggaccaaaa | 6780 |
| tcaccaccaa aactggacaa gacatgcggg tttcttccag gaagaacctt catgatcctg | 6840 |
| gcgagcccac gggagtcatt gtctgcgctt cttcttcgct gtggttacct gtttctccag | 6900 |
| ctcttctctt cgatttcttt agagatgaag ctcgtcggca tgaggtacct tgtcaaattc | 6960 |
| acacacattt aagcaaacaa gaaaagcggt ttccactcat atatttatct aacgatacat | 7020 |
| atcatcagtg ggatgctttg tcaaacggag ctcatgttca gtctattgca aacttatcca | 7080 |
| agggacaaga cagaggcaac tcagtggcaa tccaggtgcg tttattttgt cttctcctcc | 7140 |
| tctaaatctg tctaggcctt gataatctga atttctatac atttccagac agtgaaatcg | 7200 |
| agagaaaaga gcatatgggt gctgcaagac agcagcacta actcgtatga gtcggtggtg | 7260 |
| gtatacgctc ccgtagatat aaacacgaca cagctggtgc tcgcgggaca tgatccaagc | 7320 |
| aacatccaaa tcctcccctc tggattctca atcatacctg atggagtaga gtcacggcca | 7380 |
| ctggtaataa cgtctacaca agacgacaga aacagccaag gagggtcgct cctgacactc | 7440 |
| gccctccaaa ccctcatcaa cccttctcct gcagcaaagc tgaatatgga gtctgtggaa | 7500 |
| tccgtgacaa acctcgtctc agtcacacta cacaacatta agagaagtct acaaatcgaa | 7560 |
| gattgctgat gacaagtcac agcagatatt atttacctat atataattat atgataatgt | 7620 |
| atagcagcag tgcattaaag ttttgtacaa aaacgaccag ctctctcttc tccaatccta | 7680 |
| ttattatcca cacctttttt ggtccattcc attgg | 7715 |

<210> SEQ ID NO 2
<211> LENGTH: 745
<212> TYPE: PRT
<213> ORGANISM: Arabidopsis thaliana

<400> SEQUENCE: 2

Met Ala Val Asp Met Ser Ser Lys Gln Pro Thr Lys Asp Phe Phe Ser
1               5                   10                  15

Ser Pro Ala Leu Ser Leu Ser Leu Ala Gly Ile Phe Arg Asn Ala Ser
            20                  25                  30

Ser Gly Ser Thr Asn Pro Glu Glu Asp Phe Leu Gly Arg Arg Val Val
        35                  40                  45

```
Asp Asp Glu Asp Arg Thr Val Glu Met Ser Ser Glu Asn Ser Gly Pro
 50                  55                  60
Thr Arg Ser Arg Ser Glu Asp Leu Glu Gly Glu Asp His Asp Asp
 65                  70                  75                  80
Glu Glu Glu Glu Glu Asp Gly Ala Ala Gly Asn Lys Gly Thr Asn
                     85                  90                  95
Lys Arg Lys Arg Lys Lys Tyr His Arg His Thr Thr Asp Gln Ile Arg
                100                 105                 110
His Met Glu Ala Leu Phe Lys Glu Thr Pro His Pro Asp Glu Lys Gln
                115                 120                 125
Arg Gln Gln Leu Ser Lys Gln Leu Gly Leu Ala Pro Arg Gln Val Lys
    130                 135                 140
Phe Trp Phe Gln Asn Arg Arg Thr Gln Ile Lys Ala Ile Gln Glu Arg
145                 150                 155                 160
His Glu Asn Ser Leu Leu Lys Ala Glu Leu Glu Lys Leu Arg Glu Glu
                165                 170                 175
Asn Lys Ala Met Arg Glu Ser Phe Ser Lys Ala Asn Ser Ser Cys Pro
                180                 185                 190
Asn Cys Gly Gly Gly Pro Asp Asp Leu His Leu Glu Asn Ser Lys Leu
                195                 200                 205
Lys Ala Glu Leu Asp Lys Leu Arg Ala Ala Leu Gly Arg Thr Pro Tyr
    210                 215                 220
Pro Leu Gln Ala Ser Cys Ser Asp Asp Gln Glu His Arg Leu Gly Ser
225                 230                 235                 240
Leu Asp Phe Tyr Thr Gly Val Phe Ala Leu Glu Lys Ser Arg Ile Ala
                245                 250                 255
Glu Ile Ser Asn Arg Ala Thr Leu Glu Leu Gln Lys Met Ala Thr Ser
                260                 265                 270
Gly Glu Pro Met Trp Leu Arg Ser Val Glu Thr Gly Arg Glu Ile Leu
                275                 280                 285
Asn Tyr Asp Glu Tyr Leu Lys Glu Phe Pro Gln Ala Gln Ala Ser Ser
    290                 295                 300
Phe Pro Gly Arg Lys Thr Ile Glu Ala Ser Arg Asp Ala Gly Ile Val
305                 310                 315                 320
Phe Met Asp Ala His Lys Leu Ala Gln Ser Phe Met Asp Val Gly Gln
                325                 330                 335
Trp Lys Glu Thr Phe Ala Cys Leu Ile Ser Lys Ala Ala Thr Val Asp
                340                 345                 350
Val Ile Arg Gln Gly Glu Gly Pro Ser Arg Ile Asp Gly Ala Ile Gln
    355                 360                 365
Leu Met Phe Gly Glu Met Gln Leu Leu Thr Pro Val Val Pro Thr Arg
370                 375                 380
Glu Val Tyr Phe Val Arg Ser Cys Arg Gln Leu Ser Pro Glu Lys Trp
385                 390                 395                 400
Ala Ile Val Asp Val Ser Val Ser Val Glu Asp Ser Asn Thr Glu Lys
                405                 410                 415
Glu Ala Ser Leu Leu Lys Cys Arg Lys Leu Pro Ser Gly Cys Ile Ile
    420                 425                 430
Glu Asp Thr Ser Asn Gly His Ser Lys Val Thr Trp Val Glu His Leu
                435                 440                 445
Asp Val Ser Ala Ser Thr Val Gln Pro Leu Phe Arg Ser Leu Val Asn
    450                 455                 460
Thr Gly Leu Ala Phe Gly Ala Arg His Trp Val Ala Thr Leu Gln Leu
```

```
                465                 470                 475                 480
His Cys Glu Arg Leu Val Phe Phe Met Ala Thr Asn Val Pro Thr Lys
                    485                 490                 495

Asp Ser Leu Gly Val Thr Thr Leu Ala Gly Arg Lys Ser Val Leu Lys
                500                 505                 510

Met Ala Gln Arg Met Thr Gln Ser Phe Tyr Arg Ala Ile Ala Ala Ser
            515                 520                 525

Ser Tyr His Gln Trp Thr Lys Ile Thr Thr Lys Thr Gly Gln Asp Met
        530                 535                 540

Arg Val Ser Ser Arg Lys Asn Leu His Asp Pro Gly Glu Pro Thr Gly
545                 550                 555                 560

Val Ile Val Cys Ala Ser Ser Leu Trp Leu Pro Val Ser Pro Ala
                565                 570                 575

Leu Leu Phe Asp Phe Phe Arg Asp Glu Ala Arg Arg His Glu Trp Asp
                580                 585                 590

Ala Leu Ser Asn Gly Ala His Val Gln Ser Ile Ala Asn Leu Ser Lys
                595                 600                 605

Gly Gln Asp Arg Gly Asn Ser Val Ala Ile Gln Thr Val Lys Ser Arg
            610                 615                 620

Glu Lys Ser Ile Trp Val Leu Gln Asp Ser Ser Thr Asn Ser Tyr Glu
625                 630                 635                 640

Ser Val Val Val Tyr Ala Pro Val Asp Ile Asn Thr Gln Leu Val
                645                 650                 655

Leu Ala Gly His Asp Pro Ser Asn Ile Gln Ile Leu Pro Ser Gly Phe
                660                 665                 670

Ser Ile Ile Pro Asp Gly Val Glu Ser Arg Pro Leu Val Ile Thr Ser
            675                 680                 685

Thr Gln Asp Asp Arg Asn Ser Gln Gly Gly Ser Leu Leu Thr Leu Ala
        690                 695                 700

Leu Gln Thr Leu Ile Asn Pro Ser Pro Ala Ala Lys Leu Asn Met Glu
705                 710                 715                 720

Ser Val Glu Ser Val Thr Asn Leu Val Ser Val Thr Leu His Asn Ile
                725                 730                 735

Lys Arg Ser Leu Gln Ile Glu Asp Cys
                740                 745

<210> SEQ ID NO 3
<211> LENGTH: 3073
<212> TYPE: DNA
<213> ORGANISM: Zea mays
<220> FEATURE:
<221> NAME/KEY: CDS
<222> LOCATION: (270)...(2624)

<400> SEQUENCE: 3
tccatatctc agtcacacac tcacgcgcgc gcggggccg ggggccgctg gacccgccgt      60
tctccttctc ctccccccct cgttcctctc gtctcaccat tactccctac acgcgccgcg     120
gctaggattc cgccgaggag acgctgcgcg cgtggatctc cggtgctgtc ctgctagcgt     180
gcgacgaggc caggcaggcg cgcggccggc gccatgagct tcgggagcta ttcgacggcg     240
ggtccggcgg cggcggagga ggaggaggg atg cag ttc ccg ttc acg acc ggg       293
                                 Met Gln Phe Pro Phe Thr Thr Gly
                                  1               5 ttc tcg tcc tcg ccg gcc ctc tcc ctc ggt ctg gac aac gcc ggc ggc       341
Phe Ser Ser Ser Pro Ala Leu Ser Leu Gly Leu Asp Asn Ala Gly Gly
    10                  15                  20
```

-continued

```
ggc atg gtc ggc cgg atg ctc ccc gtg ggc ggc gcc ccc gcg gac ggc      389
Gly Met Val Gly Arg Met Leu Pro Val Gly Gly Ala Pro Ala Asp Gly
 25              30                  35                  40 ggg atg gcg agg gac gcc gcc gac gcc gag aac gac agc cgc tcc ggg      437
Gly Met Ala Arg Asp Ala Ala Asp Ala Glu Asn Asp Ser Arg Ser Gly
                 45                  50                  55 agc gac cac ctg gac gcc atg tcc gcc ggc gcc ggc gcc gag gac gag      485
Ser Asp His Leu Asp Ala Met Ser Ala Gly Ala Gly Ala Glu Asp Glu
             60                  65                  70 gac gac gcc gag ccg ggc aac ccg cgc aag cgc aag aag cgc tac cac      533
Asp Asp Ala Glu Pro Gly Asn Pro Arg Lys Arg Lys Lys Arg Tyr His
         75                  80                  85 cgc cac acg ccg cag cag atc cag gag ctc gaa gcg ctg ttc aag gag      581
Arg His Thr Pro Gln Gln Ile Gln Glu Leu Glu Ala Leu Phe Lys Glu
     90                  95                 100 tgc cct cac ccg gac gag aag cag cgc ggc gag ctc agc aag agg ctc      629
Cys Pro His Pro Asp Glu Lys Gln Arg Gly Glu Leu Ser Lys Arg Leu
105                 110                 115                 120 ggc ctc gac ccg cgc cag gtc aag ttc tgg ttc cag aac cgc cgc acg      677
Gly Leu Asp Pro Arg Gln Val Lys Phe Trp Phe Gln Asn Arg Arg Thr
                125                 130                 135 cgg atg aag acg caa ctg gag cgg cac gag aac gcg ctt ctc aag caa      725
Arg Met Lys Thr Gln Leu Glu Arg His Glu Asn Ala Leu Leu Lys Gln
            140                 145                 150 gag aac gac aag ctg cgg gcc gag aac atg gcg atc cgg gag gcg atg      773
Glu Asn Asp Lys Leu Arg Ala Glu Asn Met Ala Ile Arg Glu Ala Met
        155                 160                 165 cgc agc ccg atg tgc ggc agc tgc ggg agc ccc gcc atg ctc ggg gag      821
Arg Ser Pro Met Cys Gly Ser Cys Gly Ser Pro Ala Met Leu Gly Glu
    170                 175                 180 gtg tcc ctg gag gag cag cac ctg tgc atc gag aat gcg cgg ctc aag      869
Val Ser Leu Glu Glu Gln His Leu Cys Ile Glu Asn Ala Arg Leu Lys
185                 190                 195                 200 gac gag ctc aac cgc gtc tac gcc ctc gcc acc aag ttc ctc ggc aag      917
Asp Glu Leu Asn Arg Val Tyr Ala Leu Ala Thr Lys Phe Leu Gly Lys
                205                 210                 215 ccc atg ccc gtc ctc tcg ggg ccc atg ctg cag ccg aac ctg tcg ctg      965
Pro Met Pro Val Leu Ser Gly Pro Met Leu Gln Pro Asn Leu Ser Leu
            220                 225                 230 ccc atg ccg agc tcg tcg ctg gag ctg gca gta ggc ggc ctc cgt ggc     1013
Pro Met Pro Ser Ser Ser Leu Glu Leu Ala Val Gly Gly Leu Arg Gly
        235                 240                 245 cta ggg tct atc cct tcc ttg gac gag ttt gct ggc ggt gtg tct agc     1061
Leu Gly Ser Ile Pro Ser Leu Asp Glu Phe Ala Gly Gly Val Ser Ser
    250                 255                 260 ccg ttg ggc acg gtg atc acg cct gca cgg gcg acc gga tct gct ccg     1109
Pro Leu Gly Thr Val Ile Thr Pro Ala Arg Ala Thr Gly Ser Ala Pro
265                 270                 275                 280 ccg cct atg gtg ggc gtc gac agg tcc atg ctg ctg gag ctt gcg atc     1157
Pro Pro Met Val Gly Val Asp Arg Ser Met Leu Leu Glu Leu Ala Ile
                285                 290                 295 agc gcc atg gat gaa cta gtt aag ctg gca cag gtt gac gag ccc ttg     1205
Ser Ala Met Asp Glu Leu Val Lys Leu Ala Gln Val Asp Glu Pro Leu
            300                 305                 310 tgg ctt ccc agc ctc agt ggc tct ccc gac aag aag ctg ctc aac ttt     1253
Trp Leu Pro Ser Leu Ser Gly Ser Pro Asp Lys Lys Leu Leu Asn Phe
        315                 320                 325 gag gag tat gcc cac tcg ttc tct ccg tcc gtc ggc gcc gtg aag cct     1301
Glu Glu Tyr Ala His Ser Phe Ser Pro Ser Val Gly Ala Val Lys Pro
```

-continued

```
            330                 335                 340
gtg ggc tat gta tcc gag gcc tct agg gag tct ggc ctc gtc atc att    1349
Val Gly Tyr Val Ser Glu Ala Ser Arg Glu Ser Gly Leu Val Ile Ile
345                 350                 355                 360 gac aac agc ctt gct ctt gta gag acc ctt atg gac gtg aga cgg tgg    1397
Asp Asn Ser Leu Ala Leu Val Glu Thr Leu Met Asp Val Arg Arg Trp
                365                 370                 375 tct gat atg ttc tcg tgc atg att gct aag gcc aca gtc cta gag gag    1445
Ser Asp Met Phe Ser Cys Met Ile Ala Lys Ala Thr Val Leu Glu Glu
            380                 385                 390 gtg aca tct ggc att gca gga agt agg aat ggt gcg ctg ctg ctg atg    1493
Val Thr Ser Gly Ile Ala Gly Ser Arg Asn Gly Ala Leu Leu Leu Met
        395                 400                 405 aag gct gag cta cag gtg ctc tca cct cta gtg ccc atc agg gag gtc    1541
Lys Ala Glu Leu Gln Val Leu Ser Pro Leu Val Pro Ile Arg Glu Val
    410                 415                 420 aca ttt ctc agg ttt tgc aag cag ctg gct gag ggt gca tgg gca gta    1589
Thr Phe Leu Arg Phe Cys Lys Gln Leu Ala Glu Gly Ala Trp Ala Val
425                 430                 435                 440 gtg gat gtg tcc att gac gga ttg gtg aga gat cac aac tct gga aca    1637
Val Asp Val Ser Ile Asp Gly Leu Val Arg Asp His Asn Ser Gly Thr
                445                 450                 455 gca tcc aac gcc gga aat ata cgg tgc agg agg ttg cct tct ggc tgt    1685
Ala Ser Asn Ala Gly Asn Ile Arg Cys Arg Arg Leu Pro Ser Gly Cys
            460                 465                 470 gtg atg cag gac act ccc aat ggc tac tgc aag gtc aca tgg gta gag    1733
Val Met Gln Asp Thr Pro Asn Gly Tyr Cys Lys Val Thr Trp Val Glu
        475                 480                 485 tat acg gaa tac gac gag gcg tca gta cac cag ctc tat aga cca ctc    1781
Tyr Thr Glu Tyr Asp Glu Ala Ser Val His Gln Leu Tyr Arg Pro Leu
    490                 495                 500 atc cgg tcc ggg ctg gcc ttt ggg gcc agg cgg tgg ctt gca atg ctg    1829
Ile Arg Ser Gly Leu Ala Phe Gly Ala Arg Arg Trp Leu Ala Met Leu
505                 510                 515                 520 cag cgc cag tgc gaa tgc ctg gcc ata ctc atg tcc cct gat aca gtt    1877
Gln Arg Gln Cys Glu Cys Leu Ala Ile Leu Met Ser Pro Asp Thr Val
                525                 530                 535 tca gct aat gac tcg tca gtc ata aca cag gag ggc aag cga agc atg    1925
Ser Ala Asn Asp Ser Ser Val Ile Thr Gln Glu Gly Lys Arg Ser Met
            540                 545                 550 ctg aag ctg gca cgg cgg atg acg gag aac ttc tgc gcc ggg gtc agc    1973
Leu Lys Leu Ala Arg Arg Met Thr Glu Asn Phe Cys Ala Gly Val Ser
        555                 560                 565 gcg tca tct gca cgt gaa tgg agt aag ctg gac ggc gct gca ggc agc    2021
Ala Ser Ser Ala Arg Glu Trp Ser Lys Leu Asp Gly Ala Ala Gly Ser
    570                 575                 580 atc ggg gag gat gtg cgg gtc atg gca cgg aaa agc gtg gac gag cct    2069
Ile Gly Glu Asp Val Arg Val Met Ala Arg Lys Ser Val Asp Glu Pro
585                 590                 595                 600 ggg gag ccg ccg ggc gtg gtc cta agc gca cgc acg tcg gtg tgg gtg    2117
Gly Glu Pro Pro Gly Val Val Leu Ser Ala Arg Thr Ser Val Trp Val
                605                 610                 615 ccc gtg gct ccg gag aag ctc ttc aac ttc ctc cgt gac gag cag ctg    2165
Pro Val Ala Pro Glu Lys Leu Phe Asn Phe Leu Arg Asp Glu Gln Leu
            620                 625                 630 cgt gcg gag tgg gac atc ctc agc aac gga ggc ccg atg cag gag atg    2213
Arg Ala Glu Trp Asp Ile Leu Ser Asn Gly Gly Pro Met Gln Glu Met
        635                 640                 645 gcc aac atc gcc aag ggg cag gag cac ggg aac tcg gtg tcc ctc ctc    2261
```

```
Ala Asn Ile Ala Lys Gly Gln Glu His Gly Asn Ser Val Ser Leu Leu
        650                 655                 660 aga gcc agt gcc atg agt gcc aac cag agc agc atg ctg atc ctc cag    2309
Arg Ala Ser Ala Met Ser Ala Asn Gln Ser Ser Met Leu Ile Leu Gln
665                 670                 675                 680 gag act tgc act gat gca tca ggc tcg atg gtc gtg tat gct cca gtg    2357
Glu Thr Cys Thr Asp Ala Ser Gly Ser Met Val Val Tyr Ala Pro Val
                685                 690                 695 gac atc ccg gcg atg cag ctc gtc atg aac ggc ggg gac tcc acc tac    2405
Asp Ile Pro Ala Met Gln Leu Val Met Asn Gly Gly Asp Ser Thr Tyr
        700                 705                 710 gtt gct ctg ctg ccg tct ggg ttc gcc atc ctg cct gat ggc cca agc    2453
Val Ala Leu Leu Pro Ser Gly Phe Ala Ile Leu Pro Asp Gly Pro Ser
    715                 720                 725 agt gtc ggc gcc gag cac aag aca ggc ggc tcg ctg ctc acc gtc gcc    2501
Ser Val Gly Ala Glu His Lys Thr Gly Gly Ser Leu Leu Thr Val Ala
730                 735                 740 ttc cag atc ctc gtc aac agc cag ccg acc gcc aaa ctc acc gtg gag    2549
Phe Gln Ile Leu Val Asn Ser Gln Pro Thr Ala Lys Leu Thr Val Glu
745                 750                 755                 760 tca gta gag acc gtg aac aac ctc ata ttc tgc acc atc aag aag atc    2597
Ser Val Glu Thr Val Asn Asn Leu Ile Phe Cys Thr Ile Lys Lys Ile
                765                 770                 775 aag aca gcg ctg cag tgt gac gct tga ctgtcgcgtg tcgccgcagg          2644
Lys Thr Ala Leu Gln Cys Asp Ala  *
                780 gggggtggtc ggtgatgacg agcctgagtc aagaacgaac ctcgtgcggg aaagaaacct  2704 ttgctaggtg ataaggatcc agcttggacg ggtctttagc acggagcaat ggtggtggtt  2764 cgggtattga ctcggtctct gtcatctgct tcttctccat ggcaacctgt tgtctgatac  2824 gggatcttga atagtgcgtg acaatgatg tggttagatg gttaaaatct tttgtttcag   2884 tcccatcgtt tcatcaggga atcaaacttt gagttttggc cgcctcgttg ttagttgtaa  2944 tatacagttc atttatatt gtgaggtaag ctatatgcca tgtgtaaaca tgagagctca   3004 ggaatgttgg gtagcatcat gagtgtagct aggcatcgaa ctatcggcca ataaaatgtc  3064 tgatcgata                                                          3073

<210> SEQ ID NO 4
<211> LENGTH: 784
<212> TYPE: PRT
<213> ORGANISM: Zea mays

<400> SEQUENCE: 4

Met Gln Phe Pro Phe Thr Thr Gly Phe Ser Ser Ser Pro Ala Leu Ser
1               5                   10                  15

Leu Gly Leu Asp Asn Ala Gly Gly Gly Met Val Gly Arg Met Leu Pro
            20                  25                  30

Val Gly Gly Ala Pro Ala Asp Gly Gly Met Ala Arg Asp Ala Ala Asp
        35                  40                  45

Ala Glu Asn Asp Ser Arg Ser Gly Ser Asp His Leu Asp Ala Met Ser
    50                  55                  60

Ala Gly Ala Gly Ala Glu Asp Glu Asp Ala Glu Pro Gly Asn Pro
65                  70                  75                  80

Arg Lys Arg Lys Lys Arg Tyr His Arg His Thr Pro Gln Gln Ile Gln
                85                  90                  95

Glu Leu Glu Ala Leu Phe Lys Glu Cys Pro His Pro Asp Glu Lys Gln
            100                 105                 110
```

-continued

```
Arg Gly Glu Leu Ser Lys Arg Leu Gly Leu Asp Pro Arg Gln Val Lys
            115                 120                 125
Phe Trp Phe Gln Asn Arg Arg Thr Arg Met Lys Thr Gln Leu Glu Arg
130                 135                 140
His Glu Asn Ala Leu Leu Lys Gln Glu Asn Asp Lys Leu Arg Ala Glu
145                 150                 155                 160
Asn Met Ala Ile Arg Glu Ala Met Arg Ser Pro Met Cys Gly Ser Cys
                165                 170                 175
Gly Ser Pro Ala Met Leu Gly Glu Val Ser Leu Glu Glu Gln His Leu
            180                 185                 190
Cys Ile Glu Asn Ala Arg Leu Lys Asp Glu Leu Asn Arg Val Tyr Ala
            195                 200                 205
Leu Ala Thr Lys Phe Leu Gly Lys Pro Met Pro Val Leu Ser Gly Pro
            210                 215                 220
Met Leu Gln Pro Asn Leu Ser Leu Pro Met Pro Ser Ser Ser Leu Glu
225                 230                 235                 240
Leu Ala Val Gly Gly Leu Arg Gly Leu Gly Ser Ile Pro Ser Leu Asp
                245                 250                 255
Glu Phe Ala Gly Gly Val Ser Ser Pro Leu Gly Thr Val Ile Thr Pro
            260                 265                 270
Ala Arg Ala Thr Gly Ser Ala Pro Pro Met Val Gly Val Asp Arg
            275                 280                 285
Ser Met Leu Leu Glu Leu Ala Ile Ser Ala Met Asp Glu Leu Val Lys
    290                 295                 300
Leu Ala Gln Val Asp Glu Pro Leu Trp Leu Pro Ser Leu Ser Gly Ser
305                 310                 315                 320
Pro Asp Lys Lys Leu Leu Asn Phe Glu Glu Tyr Ala His Ser Phe Ser
                325                 330                 335
Pro Ser Val Gly Ala Val Lys Pro Val Gly Tyr Val Ser Glu Ala Ser
            340                 345                 350
Arg Glu Ser Gly Leu Val Ile Ile Asp Asn Ser Leu Ala Leu Val Glu
            355                 360                 365
Thr Leu Met Asp Val Arg Arg Trp Ser Asp Met Phe Ser Cys Met Ile
    370                 375                 380
Ala Lys Ala Thr Val Leu Glu Glu Val Thr Ser Gly Ile Ala Gly Ser
385                 390                 395                 400
Arg Asn Gly Ala Leu Leu Leu Met Lys Ala Glu Leu Gln Val Leu Ser
                405                 410                 415
Pro Leu Val Pro Ile Arg Glu Val Thr Phe Leu Arg Phe Cys Lys Gln
            420                 425                 430
Leu Ala Glu Gly Ala Trp Ala Val Val Asp Val Ser Ile Asp Gly Leu
            435                 440                 445
Val Arg Asp His Asn Ser Gly Thr Ala Ser Asn Ala Gly Asn Ile Arg
    450                 455                 460
Cys Arg Arg Leu Pro Ser Gly Cys Val Met Gln Asp Thr Pro Asn Gly
465                 470                 475                 480
Tyr Cys Lys Val Thr Trp Val Glu Tyr Thr Glu Tyr Asp Glu Ala Ser
                485                 490                 495
Val His Gln Leu Tyr Arg Pro Leu Ile Arg Ser Gly Leu Ala Phe Gly
            500                 505                 510
Ala Arg Arg Trp Leu Ala Met Leu Gln Arg Gln Cys Glu Cys Leu Ala
            515                 520                 525
```

```
Ile Leu Met Ser Pro Asp Thr Val Ser Ala Asn Asp Ser Ser Val Ile
        530                 535                 540

Thr Gln Glu Gly Lys Arg Ser Met Leu Lys Leu Ala Arg Arg Met Thr
545                 550                 555                 560

Glu Asn Phe Cys Ala Gly Val Ser Ala Ser Ala Arg Glu Trp Ser
                565                 570                 575

Lys Leu Asp Gly Ala Ala Gly Ser Ile Gly Glu Asp Val Arg Val Met
                580                 585                 590

Ala Arg Lys Ser Val Asp Glu Pro Gly Glu Pro Pro Gly Val Val Leu
            595                 600                 605

Ser Ala Arg Thr Ser Val Trp Val Pro Val Ala Pro Glu Lys Leu Phe
        610                 615                 620

Asn Phe Leu Arg Asp Glu Gln Leu Arg Ala Glu Trp Asp Ile Leu Ser
625                 630                 635                 640

Asn Gly Gly Pro Met Gln Glu Met Ala Asn Ile Ala Lys Gly Gln Glu
                645                 650                 655

His Gly Asn Ser Val Ser Leu Leu Arg Ala Ser Ala Met Ser Ala Asn
                660                 665                 670

Gln Ser Ser Met Leu Ile Leu Gln Glu Thr Cys Thr Asp Ala Ser Gly
            675                 680                 685

Ser Met Val Val Tyr Ala Pro Val Asp Ile Pro Ala Met Gln Leu Val
        690                 695                 700

Met Asn Gly Gly Asp Ser Thr Tyr Val Ala Leu Leu Pro Ser Gly Phe
705                 710                 715                 720

Ala Ile Leu Pro Asp Gly Pro Ser Ser Val Gly Ala Glu His Lys Thr
                725                 730                 735

Gly Gly Ser Leu Leu Thr Val Ala Phe Gln Ile Leu Val Asn Ser Gln
            740                 745                 750

Pro Thr Ala Lys Leu Thr Val Glu Ser Val Glu Thr Val Asn Asn Leu
        755                 760                 765

Ile Phe Cys Thr Ile Lys Lys Ile Lys Thr Ala Leu Gln Cys Asp Ala
        770                 775                 780

<210> SEQ ID NO 5
<211> LENGTH: 2940
<212> TYPE: DNA
<213> ORGANISM: Arabidopsis thaliana
<220> FEATURE:
<221> NAME/KEY: CDS
<222> LOCATION: (336)...(2492)

<400> SEQUENCE: 5 gtttttctt ctgaagagtg atatatattc tacctttctc tggttaaaga aactccctga      60
atccaccggt tatgtcttga ccggctttaa gcctataaac tgatgcccta agacaccttt     120
ttaggtttct caataattct ccgcatctat cttttcttct ccacaagtaa gggaaccaga    180
aaaccaggga agaatccgag caagctaggg tttcattgtg tgcacaaaat gggatataca    240
ggcagaagaa atcgagata atcaactaa atgatttgga taatcatctt gaagatttga    300
aggatttcga gactaagtcc ggcgcagaag tcacc atg gag aat cct tta gaa       353
                                    Met Glu Asn Pro Leu Glu
                                      1               5 gaa gag ctt caa gat cct aat cag cgt ccc aac aaa aag aag cgt tac      401
Glu Glu Leu Gln Asp Pro Asn Gln Arg Pro Asn Lys Lys Lys Arg Tyr
            10                  15                  20 cac cgt cac aca caa cgc cag att caa gag cta gag tcg ttc ttc aag      449
His Arg His Thr Gln Arg Gln Ile Gln Glu Leu Glu Ser Phe Phe Lys
```

```
                25                  30                  35
gaa tgt cct cat cca gac gat aag caa aga aag gag ctg agt cgc gag        497
Glu Cys Pro His Pro Asp Asp Lys Gln Arg Lys Glu Leu Ser Arg Glu
    40                  45                  50 cta agc tta gaa cct ctt caa gtc aag ttc tgg ttc caa aac aaa cgc        545
Leu Ser Leu Glu Pro Leu Gln Val Lys Phe Trp Phe Gln Asn Lys Arg
55                  60                  65                  70 act caa atg aag gca caa cat gag agg cac gag aac cag ata ctg aag        593
Thr Gln Met Lys Ala Gln His Glu Arg His Glu Asn Gln Ile Leu Lys
            75                  80                  85 tca gaa aat gac aag ctc cga gca gag aac aat agg tac aag gat gct        641
Ser Glu Asn Asp Lys Leu Arg Ala Glu Asn Asn Arg Tyr Lys Asp Ala
        90                  95                  100 cta agc aac gca aca tgc cca aac tgt ggt ggt ccg gca gct ata gga        689
Leu Ser Asn Ala Thr Cys Pro Asn Cys Gly Gly Pro Ala Ala Ile Gly
            105                 110                 115 gaa atg tcc ttc gac gaa cag cat tta agg atc gaa aat gct cgt tta        737
Glu Met Ser Phe Asp Glu Gln His Leu Arg Ile Glu Asn Ala Arg Leu
    120                 125                 130 cgc gaa gag att gac aga atc tct gcc ata gct gct aaa tac gta ggg        785
Arg Glu Glu Ile Asp Arg Ile Ser Ala Ile Ala Ala Lys Tyr Val Gly
135                 140                 145                 150 aag cct tta atg gct aat tcc tct tct ttc cct cag ctc tct tct tca        833
Lys Pro Leu Met Ala Asn Ser Ser Ser Phe Pro Gln Leu Ser Ser Ser
                155                 160                 165 cac cac att ccc tcg cgc tcg ctt gat ctt gaa gtt ggg aac ttt ggg        881
His His Ile Pro Ser Arg Ser Leu Asp Leu Glu Val Gly Asn Phe Gly
            170                 175                 180 aac aat aac aat agc cac act ggt ttc gtt ggg gaa atg ttt gga agc        929
Asn Asn Asn Asn Ser His Thr Gly Phe Val Gly Glu Met Phe Gly Ser
        185                 190                 195 agc gac att ttg agg tcg gtt tcg ata cct tct gag gct gat aag cct        977
Ser Asp Ile Leu Arg Ser Val Ser Ile Pro Ser Glu Ala Asp Lys Pro
    200                 205                 210 atg att gtt gag tta gct gtt gca gca atg gaa gag ctt gtg aga atg       1025
Met Ile Val Glu Leu Ala Val Ala Ala Met Glu Glu Leu Val Arg Met
215                 220                 225                 230 gct caa act ggt gat ccc tta tgg gtt tca agc gat aat tct gtt gag       1073
Ala Gln Thr Gly Asp Pro Leu Trp Val Ser Ser Asp Asn Ser Val Glu
                235                 240                 245 att ctc aat gaa gaa gag tat ttt agg acg ttt cct aga gga att gga       1121
Ile Leu Asn Glu Glu Glu Tyr Phe Arg Thr Phe Pro Arg Gly Ile Gly
            250                 255                 260 ccg aaa cct atc ggt ttg aga tca gaa gct tca aga gag tct act gtt       1169
Pro Lys Pro Ile Gly Leu Arg Ser Glu Ala Ser Arg Glu Ser Thr Val
        265                 270                 275 gtt atc atg aat cat atc aat ctc att gag att cta atg gat gtg aat       1217
Val Ile Met Asn His Ile Asn Leu Ile Glu Ile Leu Met Asp Val Asn
    280                 285                 290 caa tgg tct agt gtg ttc tgc ggg att gta tca aga gca ttg act cta       1265
Gln Trp Ser Ser Val Phe Cys Gly Ile Val Ser Arg Ala Leu Thr Leu
295                 300                 305                 310 gaa gtt ctc tca act ggc gta cga ggg aac tac aat ggg gca ttg caa       1313
Glu Val Leu Ser Thr Gly Val Arg Gly Asn Tyr Asn Gly Ala Leu Gln
                315                 320                 325 gtg atg aca gca gag ttc caa gtc cca tcg ccg ctt gtc cct act cgt       1361
Val Met Thr Ala Glu Phe Gln Val Pro Ser Pro Leu Val Pro Thr Arg
            330                 335                 340 gag aac tac ttt gta agg tac tgt aaa cag cac agt gac ggt att tgg       1409
```

```
Glu Asn Tyr Phe Val Arg Tyr Cys Lys Gln His Ser Asp Gly Ile Trp
        345                 350                 355 gcg gtt gtg gat gtc tct ttg gac agc cta aga cca agt ccg atc act       1457
Ala Val Val Asp Val Ser Leu Asp Ser Leu Arg Pro Ser Pro Ile Thr
360                 365                 370 aga agc aga aga aga ccc tct ggt tgt ctg att caa gaa ttg cag aat       1505
Arg Ser Arg Arg Arg Pro Ser Gly Cys Leu Ile Gln Glu Leu Gln Asn
375                 380                 385                 390 ggt tac tcc aag gtg aca tgg gta gag cat att gag gtg gat gat aga       1553
Gly Tyr Ser Lys Val Thr Trp Val Glu His Ile Glu Val Asp Asp Arg
            395                 400                 405 tcg gtt cac aac atg tat aaa ccg ttg gtt aat acc ggt tta gct ttc       1601
Ser Val His Asn Met Tyr Lys Pro Leu Val Asn Thr Gly Leu Ala Phe
                410                 415                 420 ggt gca aaa cgt tgg gtg gct aca ctt gac cgc caa tgt gag cgg ctc       1649
Gly Ala Lys Arg Trp Val Ala Thr Leu Asp Arg Gln Cys Glu Arg Leu
            425                 430                 435 gcc agt tcc atg gcc agc aac att ccg gct tgt gat ctt tcc gtg ata       1697
Ala Ser Ser Met Ala Ser Asn Ile Pro Ala Cys Asp Leu Ser Val Ile
                440                 445                 450 acg agt cct gag ggg aga aag agc atg ctg aaa cta gcg gag aga atg       1745
Thr Ser Pro Glu Gly Arg Lys Ser Met Leu Lys Leu Ala Glu Arg Met
455                 460                 465                 470 gtg atg agc ttc tgt acc gga gtc ggc gcg tca acc gcc gat gcc tgg       1793
Val Met Ser Phe Cys Thr Gly Val Gly Ala Ser Thr Ala Asp Ala Trp
            475                 480                 485 act aca ttg tcg acc aca gga tcc gac gac gtt cgg gtc atg acc cga       1841
Thr Thr Leu Ser Thr Thr Gly Ser Asp Asp Val Arg Val Met Thr Arg
                490                 495                 500 aag agc atg gat gat ccg gga aga cct cca ggc atc gtt ctc agc gcc       1889
Lys Ser Met Asp Asp Pro Gly Arg Pro Pro Gly Ile Val Leu Ser Ala
            505                 510                 515 gct act tct ttc tgg atc cct gta gct cca aaa cga gtg ttc gat ttt       1937
Ala Thr Ser Phe Trp Ile Pro Val Ala Pro Lys Arg Val Phe Asp Phe
520                 525                 530 ctc aga gat gaa aac tca aga agc gag tgg gat ata ctt tcc aat gga       1985
Leu Arg Asp Glu Asn Ser Arg Ser Glu Trp Asp Ile Leu Ser Asn Gly
535                 540                 545                 550 ggc ttg gtt caa gaa atg gct cat atc gca aat ggt cgt gat cct ggg       2033
Gly Leu Val Gln Glu Met Ala His Ile Ala Asn Gly Arg Asp Pro Gly
                555                 560                 565 aat agt gtc tcc ttg ctt cga gtc aat agt ggg aac tca ggg cag agc       2081
Asn Ser Val Ser Leu Leu Arg Val Asn Ser Gly Asn Ser Gly Gln Ser
            570                 575                 580 aac atg ttg atc tta caa gaa agt tgt acg gac gca tca ggg tcc tat       2129
Asn Met Leu Ile Leu Gln Glu Ser Cys Thr Asp Ala Ser Gly Ser Tyr
                585                 590                 595 gtg ata tac gca cca gtt gat ata ata gct atg aac gtt gtc ctg agt       2177
Val Ile Tyr Ala Pro Val Asp Ile Ile Ala Met Asn Val Val Leu Ser
            600                 605                 610 ggt ggt gat ccg gat tat gtc gct ttg tta cca tcc gga ttc gct att       2225
Gly Gly Asp Pro Asp Tyr Val Ala Leu Leu Pro Ser Gly Phe Ala Ile
615                 620                 625                 630 ttg ccg gat ggc tct gct aga gga gga gga ggt agt gct aat gcc agt       2273
Leu Pro Asp Gly Ser Ala Arg Gly Gly Gly Gly Ser Ala Asn Ala Ser
            635                 640                 645 gct gga gcc gga gtt gaa gga gga gga gag ggg aat aat ctt gaa gtg       2321
Ala Gly Ala Gly Val Glu Gly Gly Gly Glu Gly Asn Asn Leu Glu Val
                650                 655                 660
```

```
gtt act act act ggg agt tgt ggc ggt tca cta ctc aca gtt gcg ttt       2369
Val Thr Thr Thr Gly Ser Cys Gly Gly Ser Leu Leu Thr Val Ala Phe
            665                 670                 675 cag ata ctt gtt gac tct gtt cct acc gct aaa ctc tct ctc ggt tca       2417
Gln Ile Leu Val Asp Ser Val Pro Thr Ala Lys Leu Ser Leu Gly Ser
        680                 685                 690 gtt gct aca gtc aat agt ctg atc aaa tgc act gtc gag cgg att aaa       2465
Val Ala Thr Val Asn Ser Leu Ile Lys Cys Thr Val Glu Arg Ile Lys
695                 700                 705                 710 gcc gct ctg gcc tgc gac gga gcc taa tcgatgtttt cggaaggtaa             2512
Ala Ala Leu Ala Cys Asp Gly Ala  *
                715 gagtgaaagg ggaggtttag ggagtttatg ataatgtttg tgttcttttg gtttttaaag     2572 tcttttgaga ttctccaaag gaagtcaaga acgctccttt tgcgtttaa tctcatttcc      2632 gcgtttgtta gcggacgggc caaagaaaga ggcttgagaa agaaaaggta agaggttcg      2692 ggtattgact tctgctggaa ccaaaaaaaa aggaatcggg tttgttgtgt ttcggcggtt     2752 tagcattttg cgttttcttt gttattattt atcattgact agtgaacagt ttagcgttct    2812 gcttttcgcg tctactgtga aactccttgt tattaagcca ctctagtggt actgtcatta    2872 tatattatga atctatgaaa ctgtgtttat tagtttgttt ctttaatcca aacttgagat    2932 tctcttct                                                              2940

<210> SEQ ID NO 6
<211> LENGTH: 718
<212> TYPE: PRT
<213> ORGANISM: Arabidopsis thaliana

<400> SEQUENCE: 6

Met Glu Asn Pro Leu Glu Glu Leu Gln Asp Pro Asn Gln Arg Pro
1               5                   10                  15

Asn Lys Lys Arg Tyr His Arg His Thr Gln Arg Gln Ile Gln Glu
            20                  25                  30

Leu Glu Ser Phe Phe Lys Glu Cys Pro His Pro Asp Asp Lys Gln Arg
        35                  40                  45

Lys Glu Leu Ser Arg Glu Leu Ser Leu Glu Pro Leu Gln Val Lys Phe
    50                  55                  60

Trp Phe Gln Asn Lys Arg Thr Gln Met Lys Ala Gln His Glu Arg His
65                  70                  75                  80

Glu Asn Gln Ile Leu Lys Ser Glu Asn Asp Lys Leu Arg Ala Glu Asn
                85                  90                  95

Asn Arg Tyr Lys Asp Ala Leu Ser Asn Ala Thr Cys Pro Asn Cys Gly
            100                 105                 110

Gly Pro Ala Ala Ile Gly Glu Met Ser Phe Asp Glu Gln His Leu Arg
        115                 120                 125

Ile Glu Asn Ala Arg Leu Arg Glu Glu Ile Asp Arg Ile Ser Ala Ile
    130                 135                 140

Ala Ala Lys Tyr Val Gly Lys Pro Leu Met Ala Asn Ser Ser Ser Phe
145                 150                 155                 160

Pro Gln Leu Ser Ser Ser His His Ile Pro Ser Arg Ser Leu Asp Leu
                165                 170                 175

Glu Val Gly Asn Phe Gly Asn Asn Asn Ser His Thr Gly Phe Val
            180                 185                 190

Gly Glu Met Phe Gly Ser Ser Asp Ile Leu Arg Ser Val Ser Ile Pro
        195                 200                 205
```

-continued

```
Ser Glu Ala Asp Lys Pro Met Ile Val Glu Leu Ala Val Ala Ala Met
210                 215                 220
Glu Glu Leu Val Arg Met Ala Gln Thr Gly Asp Pro Leu Trp Val Ser
225                 230                 235                 240
Ser Asp Asn Ser Val Glu Ile Leu Asn Glu Glu Tyr Phe Arg Thr
            245                 250                 255
Phe Pro Arg Gly Ile Gly Pro Lys Pro Ile Gly Leu Arg Ser Glu Ala
                260                 265                 270
Ser Arg Glu Ser Thr Val Val Ile Met Asn His Ile Asn Leu Ile Glu
            275                 280                 285
Ile Leu Met Asp Val Asn Gln Trp Ser Ser Val Phe Cys Gly Ile Val
290                 295                 300
Ser Arg Ala Leu Thr Leu Glu Val Leu Ser Thr Gly Val Arg Gly Asn
305                 310                 315                 320
Tyr Asn Gly Ala Leu Gln Val Met Thr Ala Glu Phe Gln Val Pro Ser
                325                 330                 335
Pro Leu Val Pro Thr Arg Glu Asn Tyr Phe Val Arg Tyr Cys Lys Gln
            340                 345                 350
His Ser Asp Gly Ile Trp Ala Val Val Asp Val Ser Leu Asp Ser Leu
            355                 360                 365
Arg Pro Ser Pro Ile Thr Arg Ser Arg Arg Pro Ser Gly Cys Leu
370                 375                 380
Ile Gln Glu Leu Gln Asn Gly Tyr Ser Lys Val Thr Trp Val Glu His
385                 390                 395                 400
Ile Glu Val Asp Asp Arg Ser Val His Asn Met Tyr Lys Pro Leu Val
                405                 410                 415
Asn Thr Gly Leu Ala Phe Gly Ala Lys Arg Trp Val Ala Thr Leu Asp
            420                 425                 430
Arg Gln Cys Glu Arg Leu Ala Ser Ser Met Ala Ser Asn Ile Pro Ala
        435                 440                 445
Cys Asp Leu Ser Val Ile Thr Ser Pro Glu Gly Arg Lys Ser Met Leu
    450                 455                 460
Lys Leu Ala Glu Arg Met Val Met Ser Phe Cys Thr Gly Val Gly Ala
465                 470                 475                 480
Ser Thr Ala Asp Ala Trp Thr Thr Leu Ser Thr Thr Gly Ser Asp Asp
                485                 490                 495
Val Arg Val Met Thr Arg Lys Ser Met Asp Asp Pro Gly Arg Pro Pro
            500                 505                 510
Gly Ile Val Leu Ser Ala Ala Thr Ser Phe Trp Ile Pro Val Ala Pro
    515                 520                 525
Lys Arg Val Phe Asp Phe Leu Arg Asp Glu Asn Ser Arg Ser Glu Trp
530                 535                 540
Asp Ile Leu Ser Asn Gly Gly Leu Val Gln Glu Met Ala His Ile Ala
545                 550                 555                 560
Asn Gly Arg Asp Pro Gly Asn Ser Val Ser Leu Leu Arg Val Asn Ser
                565                 570                 575
Gly Asn Ser Gly Gln Ser Asn Met Leu Ile Leu Gln Glu Ser Cys Thr
            580                 585                 590
Asp Ala Ser Gly Ser Tyr Val Ile Tyr Ala Pro Val Asp Ile Ile Ala
        595                 600                 605
Met Asn Val Val Leu Ser Gly Gly Asp Pro Asp Tyr Val Ala Leu Leu
    610                 615                 620
Pro Ser Gly Phe Ala Ile Leu Pro Asp Gly Ser Ala Arg Gly Gly Gly
```

-continued

```
            625                 630                 635                 640
Gly Ser Ala Asn Ala Ser Ala Gly Ala Gly Val Glu Gly Gly Glu
                645                 650                 655
Gly Asn Asn Leu Glu Val Val Thr Thr Thr Gly Ser Cys Gly Gly Ser
            660                 665                 670
Leu Leu Thr Val Ala Phe Gln Ile Leu Val Asp Ser Val Pro Thr Ala
        675                 680                 685
Lys Leu Ser Leu Gly Ser Val Ala Thr Val Asn Ser Leu Ile Lys Cys
    690                 695                 700
Thr Val Glu Arg Ile Lys Ala Ala Leu Ala Cys Asp Gly Ala
705                 710                 715

<210> SEQ ID NO 7
<211> LENGTH: 2953
<212> TYPE: DNA
<213> ORGANISM: Arabidopsis thaliana
<220> FEATURE:
<221> NAME/KEY: CDS
<222> LOCATION: (325)...(2562)

<400> SEQUENCE: 7
aattcgcggc cgctctcttt ctctctcctc catttcagta ataaacactc cttcctcttt      60 aattttctg ggtttcttct tcttccctct tttgttgttt ctgtgtgatt cagttctcga     120
tccatctttt cgtgaaaagt atcaatcttt taattctcta gttgtttgtc aaatctggtt     180
agtttcttct cttgtattta tttgatgaac ttcggtagtc tcttcgataa cacacccggt     240
ggtggctcta ccggagcaag acttctctcc ggtttaagtt atggcaacca caccgccgca     300
actaacgtct tacccggtgg tgct atg gct caa gcg gca gcg gct gct agt       351
                          Met Ala Gln Ala Ala Ala Ala Ala Ser
                            1               5 ctc ttc tct cct cct cta acg aaa tct gtt tac gct tct tct ggc ctc      399
Leu Phe Ser Pro Pro Leu Thr Lys Ser Val Tyr Ala Ser Ser Gly Leu
 10                  15                  20                  25 tct cta gcc ctc gag caa ccg gag aga gga acc aac cgt gga gaa gca      447
Ser Leu Ala Leu Glu Gln Pro Glu Arg Gly Thr Asn Arg Gly Glu Ala
                 30                  35                  40 tcg atg agg aac aat aat aac gtc gga gga gga ggc gat act ttc gat      495
Ser Met Arg Asn Asn Asn Asn Val Gly Gly Gly Gly Asp Thr Phe Asp
             45                  50                  55 ggg agt gtg aac aga aga agc cga gaa gaa gaa cat gag agt aga tct      543
Gly Ser Val Asn Arg Arg Ser Arg Glu Glu Glu His Glu Ser Arg Ser
         60                  65                  70 ggt agt gat aac gtt gaa ggt atc tcc ggt gaa gat caa gac gct gct      591
Gly Ser Asp Asn Val Glu Gly Ile Ser Gly Glu Asp Gln Asp Ala Ala
     75                  80                  85 gat aag cct cct cgg aag aaa cgt tat cac cga cac act cct caa caa      639
Asp Lys Pro Pro Arg Lys Lys Arg Tyr His Arg His Thr Pro Gln Gln
 90                  95                 100                 105 atc caa gaa ctc gaa tct atg ttc aaa gag tgt ccg cat cca gac gag      687
Ile Gln Glu Leu Glu Ser Met Phe Lys Glu Cys Pro His Pro Asp Glu
                110                 115                 120 aaa caa aga tta gaa cta agt aag aga ctt tgc tta gag aca aga caa      735
Lys Gln Arg Leu Glu Leu Ser Lys Arg Leu Cys Leu Glu Thr Arg Gln
            125                 130                 135 gtc aag ttc tgg ttc cag aat cgt cgc act cag atg aag act caa tta      783
Val Lys Phe Trp Phe Gln Asn Arg Arg Thr Gln Met Lys Thr Gln Leu
        140                 145                 150 gag agg cat gag aac gcg tta ttg aga caa gag aac gat aag tta aga      831
```

```
Glu Arg His Glu Asn Ala Leu Leu Arg Gln Glu Asn Asp Lys Leu Arg
    155                 160                 165 gct gag aac atg tct att cgt gaa gca atg agg aat cca atc tgc acc    879
Ala Glu Asn Met Ser Ile Arg Glu Ala Met Arg Asn Pro Ile Cys Thr
170                 175                 180                 185 aat tgt ggt gga cct gcc atg ctt ggt gat gtc tct ctt gaa gaa cat    927
Asn Cys Gly Gly Pro Ala Met Leu Gly Asp Val Ser Leu Glu Glu His
                190                 195                 200 cat ctc cgt atc gaa aac gct cgt tta aaa gac gag ctt gat cgt gtc    975
His Leu Arg Ile Glu Asn Ala Arg Leu Lys Asp Glu Leu Asp Arg Val
            205                 210                 215 tgt aac ctc acc ggt aag ttc ctt ggc cac cac cat aat cac cac tac   1023
Cys Asn Leu Thr Gly Lys Phe Leu Gly His His His Asn His His Tyr
        220                 225                 230 aac tcc tcc tta gaa ctc gct gtc ggc acc aac aac aac ggt gga cat   1071
Asn Ser Ser Leu Glu Leu Ala Val Gly Thr Asn Asn Asn Gly Gly His
    235                 240                 245 ttc gct ttc cct cct gat ttc ggc ggt ggt ggt tgc tta cct ccg       1119
Phe Ala Phe Pro Pro Asp Phe Gly Gly Gly Gly Cys Leu Pro Pro
250                 255                 260                 265 cag cag cag cag tcg acg gtg att aat ggg att gat cag aag tca gtt   1167
Gln Gln Gln Gln Ser Thr Val Ile Asn Gly Ile Asp Gln Lys Ser Val
                270                 275                 280 ttg ctg gag ctg gct tta act gct atg gat gag tta gtg aag ctt gct   1215
Leu Leu Glu Leu Ala Leu Thr Ala Met Asp Glu Leu Val Lys Leu Ala
            285                 290                 295 cag agt gaa gaa ccg tta tgg gtc aaa agc ttg gac ggt gag aga gac   1263
Gln Ser Glu Glu Pro Leu Trp Val Lys Ser Leu Asp Gly Glu Arg Asp
        300                 305                 310 gag ctt aac caa gat gag tac atg aga aca ttt tca tct act aaa cca   1311
Glu Leu Asn Gln Asp Glu Tyr Met Arg Thr Phe Ser Ser Thr Lys Pro
    315                 320                 325 acc ggt tta gct act gaa gct tct aga acc tct ggt atg gtc atc atc   1359
Thr Gly Leu Ala Thr Glu Ala Ser Arg Thr Ser Gly Met Val Ile Ile
330                 335                 340                 345 aat agc tta gct ctc gtc gag act tta atg gac tcc aat cgg tgg acg   1407
Asn Ser Leu Ala Leu Val Glu Thr Leu Met Asp Ser Asn Arg Trp Thr
                350                 355                 360 gag atg ttc ccg tgt aac gtc gca aga gct aca acc acc gac gtt ata   1455
Glu Met Phe Pro Cys Asn Val Ala Arg Ala Thr Thr Thr Asp Val Ile
            365                 370                 375 tcc ggt ggg atg gct gga aca ata aat ggt gca ctt caa ctg atg aat   1503
Ser Gly Gly Met Ala Gly Thr Ile Asn Gly Ala Leu Gln Leu Met Asn
        380                 385                 390 gca gag cta caa gtt ttg tct cca ctg gtt ccg gtt cgt aat gtt aat   1551
Ala Glu Leu Gln Val Leu Ser Pro Leu Val Pro Val Arg Asn Val Asn
    395                 400                 405 ttc ctc cgg ttc tgc aaa cag cac gcg gag ggt gtg tgg gcg gtg gtg   1599
Phe Leu Arg Phe Cys Lys Gln His Ala Glu Gly Val Trp Ala Val Val
410                 415                 420                 425 gat gta tca att gat cct gtc agg gaa aac tct ggt ggt gcc ccg gta   1647
Asp Val Ser Ile Asp Pro Val Arg Glu Asn Ser Gly Gly Ala Pro Val
                430                 435                 440 atc cgg cga cta cca tca gga tgt gtg gtg cag gat gtg tct aat gga   1695
Ile Arg Arg Leu Pro Ser Gly Cys Val Val Gln Asp Val Ser Asn Gly
            445                 450                 455 tac tct aag gtc acg tgg gtg gag cat gca gaa tac gac gag aac caa   1743
Tyr Ser Lys Val Thr Trp Val Glu His Ala Glu Tyr Asp Glu Asn Gln
        460                 465                 470
```

```
atc cac cag ctg tac agg ccg ttg cta cgg tca ggc ctt ggt ttt ggc    1791
Ile His Gln Leu Tyr Arg Pro Leu Leu Arg Ser Gly Leu Gly Phe Gly
    475                 480                 485 tct caa aga tgg ctc gct aca ctt cag aga cag tgc gag tgt ctc gcc    1839
Ser Gln Arg Trp Leu Ala Thr Leu Gln Arg Gln Cys Glu Cys Leu Ala
490                 495                 500                 505 atc ctc att tct tcc tcc gtt aca tct cac gac aac aca tca ata acg    1887
Ile Leu Ile Ser Ser Ser Val Thr Ser His Asp Asn Thr Ser Ile Thr
                510                 515                 520 ctt ggt ggt cga aaa agc atg ctg aag tta gct caa cgc atg acg ttc    1935
Leu Gly Gly Arg Lys Ser Met Leu Lys Leu Ala Gln Arg Met Thr Phe
            525                 530                 535 aac ttc tgt tcg gga att tcg gcg ccg tcg gtc cac aat tgg agc aag    1983
Asn Phe Cys Ser Gly Ile Ser Ala Pro Ser Val His Asn Trp Ser Lys
        540                 545                 550 ctc act gtt gga aat gtt gac ccg gac gtt cga gtt atg acc cgt aag    2031
Leu Thr Val Gly Asn Val Asp Pro Asp Val Arg Val Met Thr Arg Lys
    555                 560                 565 agt gtg gac gat cca gga gag cct ccg ggg att gtt ttg agt gct gcc    2079
Ser Val Asp Asp Pro Gly Glu Pro Pro Gly Ile Val Leu Ser Ala Ala
570                 575                 580                 585 act tct gtt tgg cta cct gct gca cca cag cgt ctg tat gat ttc ttg    2127
Thr Ser Val Trp Leu Pro Ala Ala Pro Gln Arg Leu Tyr Asp Phe Leu
                590                 595                 600 cgg aac gaa cgg atg aga tgc gaa tgg gat att cta tcc aac ggt ggt    2175
Arg Asn Glu Arg Met Arg Cys Glu Trp Asp Ile Leu Ser Asn Gly Gly
            605                 610                 615 ccc atg cag gag atg gcc cat atc acc aaa ggt caa gat cag ggt gtc    2223
Pro Met Gln Glu Met Ala His Ile Thr Lys Gly Gln Asp Gln Gly Val
        620                 625                 630 tct ctg ctc cgc tcc aat gca atg aac gcg aat cag agt agt atg cta    2271
Ser Leu Leu Arg Ser Asn Ala Met Asn Ala Asn Gln Ser Ser Met Leu
    635                 640                 645 att ctt cag gag aca tgc att gac gca tct gga gcg ctt gta gta tac    2319
Ile Leu Gln Glu Thr Cys Ile Asp Ala Ser Gly Ala Leu Val Val Tyr
650                 655                 660                 665 gcg cct gtc gac att ccc gcc atg cat gtg gtg atg aac ggt ggt gat    2367
Ala Pro Val Asp Ile Pro Ala Met His Val Val Met Asn Gly Gly Asp
                670                 675                 680 tca tcc tac gtg gct ctc ctt ccg tcc ggt ttc gct gtt ctt cct gac    2415
Ser Ser Tyr Val Ala Leu Leu Pro Ser Gly Phe Ala Val Leu Pro Asp
            685                 690                 695 gga ggc att gac ggt ggt ggg tca ggt gat ggt gac cag cga ccg gtt    2463
Gly Gly Ile Asp Gly Gly Gly Ser Gly Asp Gly Asp Gln Arg Pro Val
        700                 705                 710 ggt ggt gga tcc ctc ttg aca gtg gcg ttt caa atc ctt gta aac atc    2511
Gly Gly Gly Ser Leu Leu Thr Val Ala Phe Gln Ile Leu Val Asn Ile
    715                 720                 725 tcc caa cgg caa aac tca cgg ttg agt cgg tgg aga ctg tca aca acc    2559
Ser Gln Arg Gln Asn Ser Arg Leu Ser Arg Trp Arg Leu Ser Thr Thr
730                 735                 740                 745 taa tatcatgcac cgttcagaag attcgtgccg ctttacaatg cgaaagctga         2612
 * tcttgatcaa gactggcgcg tgcgtgtgtt tcttttttctt aatgaattgt gaatttttat    2672
ataacttgtt tttttggtct tgtactatgg gagggagggg gtgtcgagtc aagaacgaac    2732
cgcgcgagtg ggcgagatcc aactcctttg tcaccgtgat gggacaacga cgtaaaaggg    2792
ttcgggtccg atcacggtgg aggagttggt ggttcgggta ttgactgggg tttggaaacc    2852
```

```
cctctcttac tcttttttgtt tgtgtttgtt attttttatta tgtagcgcga gtaagccaca    2912
cgcgtggggt gtgttgtggt tagaaaacgc gaactgtgag g                          2953
```

<210> SEQ ID NO 8
<211> LENGTH: 745
<212> TYPE: PRT
<213> ORGANISM: Arabidopsis thaliana

<400> SEQUENCE: 8

```
Met Ala Gln Ala Ala Ala Ala Ser Leu Phe Ser Pro Pro Leu Thr
 1               5                  10                  15

Lys Ser Val Tyr Ala Ser Ser Gly Leu Ser Leu Ala Leu Glu Gln Pro
                20                  25                  30

Glu Arg Gly Thr Asn Arg Gly Glu Ala Ser Met Arg Asn Asn Asn Asn
            35                  40                  45

Val Gly Gly Gly Gly Asp Thr Phe Asp Gly Ser Val Asn Arg Arg Ser
        50                  55                  60

Arg Glu Glu Glu His Glu Ser Arg Ser Gly Ser Asp Asn Val Glu Gly
65                  70                  75                  80

Ile Ser Gly Glu Asp Gln Asp Ala Ala Asp Lys Pro Pro Arg Lys Lys
                85                  90                  95

Arg Tyr His Arg His Thr Pro Gln Gln Ile Gln Glu Leu Glu Ser Met
            100                 105                 110

Phe Lys Glu Cys Pro His Pro Asp Glu Lys Gln Arg Leu Glu Leu Ser
        115                 120                 125

Lys Arg Leu Cys Leu Glu Thr Arg Gln Val Lys Phe Trp Phe Gln Asn
130                 135                 140

Arg Arg Thr Gln Met Lys Thr Gln Leu Glu Arg His Glu Asn Ala Leu
145                 150                 155                 160

Leu Arg Gln Glu Asn Asp Lys Leu Arg Ala Glu Asn Met Ser Ile Arg
                165                 170                 175

Glu Ala Met Arg Asn Pro Ile Cys Thr Asn Cys Gly Gly Pro Ala Met
            180                 185                 190

Leu Gly Asp Val Ser Leu Glu His His Leu Arg Ile Glu Asn Ala
        195                 200                 205

Arg Leu Lys Asp Glu Leu Asp Arg Val Cys Asn Leu Thr Gly Lys Phe
210                 215                 220

Leu Gly His His His Asn His His Tyr Asn Ser Ser Leu Glu Leu Ala
225                 230                 235                 240

Val Gly Thr Asn Asn Asn Gly Gly His Phe Ala Phe Pro Pro Asp Phe
                245                 250                 255

Gly Gly Gly Gly Gly Cys Leu Pro Pro Gln Gln Gln Ser Thr Val
            260                 265                 270

Ile Asn Gly Ile Asp Gln Lys Ser Val Leu Leu Glu Leu Ala Leu Thr
        275                 280                 285

Ala Met Asp Glu Leu Val Lys Leu Ala Gln Ser Glu Glu Pro Leu Trp
290                 295                 300

Val Lys Ser Leu Asp Gly Glu Arg Asp Glu Leu Asn Gln Asp Glu Tyr
305                 310                 315                 320

Met Arg Thr Phe Ser Ser Thr Lys Pro Thr Gly Leu Ala Thr Glu Ala
                325                 330                 335

Ser Arg Thr Ser Gly Met Val Ile Ile Asn Ser Leu Ala Leu Val Glu
            340                 345                 350

Thr Leu Met Asp Ser Asn Arg Trp Thr Glu Met Phe Pro Cys Asn Val
```

355                 360                 365
Ala Arg Ala Thr Thr Thr Asp Val Ile Ser Gly Gly Met Ala Gly Thr
370                 375                 380

Ile Asn Gly Ala Leu Gln Leu Met Asn Ala Glu Leu Gln Val Leu Ser
385                 390                 395                 400

Pro Leu Val Pro Val Arg Asn Val Asn Phe Leu Arg Phe Cys Lys Gln
                405                 410                 415

His Ala Glu Gly Val Trp Ala Val Val Asp Val Ser Ile Asp Pro Val
            420                 425                 430

Arg Glu Asn Ser Gly Gly Ala Pro Val Ile Arg Arg Leu Pro Ser Gly
        435                 440                 445

Cys Val Val Gln Asp Val Ser Asn Gly Tyr Ser Lys Val Thr Trp Val
    450                 455                 460

Glu His Ala Glu Tyr Asp Glu Asn Gln Ile His Gln Leu Tyr Arg Pro
465                 470                 475                 480

Leu Leu Arg Ser Gly Leu Gly Phe Gly Ser Gln Arg Trp Leu Ala Thr
                485                 490                 495

Leu Gln Arg Gln Cys Glu Cys Leu Ala Ile Leu Ile Ser Ser Ser Val
            500                 505                 510

Thr Ser His Asp Asn Thr Ser Ile Thr Leu Gly Gly Arg Lys Ser Met
        515                 520                 525

Leu Lys Leu Ala Gln Arg Met Thr Phe Asn Phe Cys Ser Gly Ile Ser
    530                 535                 540

Ala Pro Ser Val His Asn Trp Ser Lys Leu Thr Val Gly Asn Val Asp
545                 550                 555                 560

Pro Asp Val Arg Val Met Thr Arg Lys Ser Val Asp Asp Pro Gly Glu
                565                 570                 575

Pro Pro Gly Ile Val Leu Ser Ala Ala Thr Ser Val Trp Leu Pro Ala
            580                 585                 590

Ala Pro Gln Arg Leu Tyr Asp Phe Leu Arg Asn Glu Arg Met Arg Cys
        595                 600                 605

Glu Trp Asp Ile Leu Ser Asn Gly Gly Pro Met Gln Glu Met Ala His
    610                 615                 620

Ile Thr Lys Gly Gln Asp Gln Gly Val Ser Leu Leu Arg Ser Asn Ala
625                 630                 635                 640

Met Asn Ala Asn Gln Ser Ser Met Leu Ile Leu Gln Glu Thr Cys Ile
                645                 650                 655

Asp Ala Ser Gly Ala Leu Val Val Tyr Ala Pro Val Asp Ile Pro Ala
            660                 665                 670

Met His Val Val Met Asn Gly Gly Asp Ser Ser Tyr Val Ala Leu Leu
        675                 680                 685

Pro Ser Gly Phe Ala Val Leu Pro Asp Gly Ile Asp Gly Gly Gly
    690                 695                 700

Ser Gly Asp Gly Asp Gln Arg Pro Val Gly Gly Ser Leu Leu Thr
705                 710                 715                 720

Val Ala Phe Gln Ile Leu Val Asn Ile Ser Gln Arg Gln Asn Ser Arg
                725                 730                 735

Leu Ser Arg Trp Arg Leu Ser Thr Thr
            740                 745

<210> SEQ ID NO 9
<211> LENGTH: 3060
<212> TYPE: DNA
<213> ORGANISM: Phalaenopsis sp.

```
<220> FEATURE:
<221> NAME/KEY: CDS
<222> LOCATION: (291)...(2597)

<400> SEQUENCE: 9
cttgttcctc acccctttcct cttcccttc cctgcaaccc ttttcagctt ccatggcatc      60
ctctttttct ctgtatcgac ttcatcttct ctcacctctg catgcactca cgtagatctt     120
agctcttcta tccattcctc cttatttttc tcagctttct ggtgatatat tgttcttta      180 acttttcttc tctctaactg agctctgaag aaatggagaa accaaagaaa ggttgcagtg     240
aacggaatcc catgagtggg agaagaaatt agggtttgtt ggagcaaaat atg ctt       296
                                                        Met Leu
                                                          1 gcc ggc gtc atg att ccg gca aga cag gta cct tcg atg atc ggc agg     344
Ala Gly Val Met Ile Pro Ala Arg Gln Val Pro Ser Met Ile Gly Arg
      5                  10                  15 aac tct tca gcg ttg acc tta gct cag atc aat atc ttg gaa ggc caa     392
Asn Ser Ser Ala Leu Thr Leu Ala Gln Ile Asn Ile Leu Glu Gly Gln
 20                  25                  30 caa ctc cct ctt cag cac caa ctc gcc gaa ctg acg gca caa gcg acg     440
Gln Leu Pro Leu Gln His Gln Leu Ala Glu Leu Thr Ala Gln Ala Thr
 35                  40                  45                  50 acg acg gcg gag agt gac atg atg agg gct cga gaa gac gac ttc gag     488
Thr Thr Ala Glu Ser Asp Met Met Arg Ala Arg Glu Asp Asp Phe Glu
             55                  60                  65 agc aag tcc ggc agc gat aac atc gag ggc ggc tcc ggc gat gaa cac     536
Ser Lys Ser Gly Ser Asp Asn Ile Glu Gly Gly Ser Gly Asp Glu His
         70                  75                  80 gat ccc aat cag cga ccg agg aag aag aga tac cac agg cac act cag     584
Asp Pro Asn Gln Arg Pro Arg Lys Lys Arg Tyr His Arg His Thr Gln
     85                  90                  95 cac caa att cag gaa atg gaa gct ttt ttt aag gaa tgc ccg cat ccg     632
His Gln Ile Gln Glu Met Glu Ala Phe Phe Lys Glu Cys Pro His Pro
100                 105                 110 gat gac aag cag aga aag gcg ctc agt aag gag ctg gga ttg gaa cca     680
Asp Asp Lys Gln Arg Lys Ala Leu Ser Lys Glu Leu Gly Leu Glu Pro
115                 120                 125                 130 cta caa gtg aag ttt tgg ttt cag aac aag cgc acg caa atg aag aca     728
Leu Gln Val Lys Phe Trp Phe Gln Asn Lys Arg Thr Gln Met Lys Thr
                135                 140                 145 cag cat gac aga caa gag aat tca cag ctt agg gca gag aac gat aag     776
Gln His Asp Arg Gln Glu Asn Ser Gln Leu Arg Ala Glu Asn Asp Lys
            150                 155                 160 ctg cgg aat gaa aac ctg cgg tat aag gaa gca ctg agc aat gcc tca     824
Leu Arg Asn Glu Asn Leu Arg Tyr Lys Glu Ala Leu Ser Asn Ala Ser
        165                 170                 175 tgc cct aac tgc ggc ggc cca gct aca ctt ggg gag atg tcg ttt gac     872
Cys Pro Asn Cys Gly Gly Pro Ala Thr Leu Gly Glu Met Ser Phe Asp
    180                 185                 190 gag cac cac ctc agg att gag aac gcc agg ctg aga gaa gag ata gac     920
Glu His His Leu Arg Ile Glu Asn Ala Arg Leu Arg Glu Glu Ile Asp
195                 200                 205                 210 agg atc tcc ggc att gct gca aaa tac gta ggc aag cca atg aac tca     968
Arg Ile Ser Gly Ile Ala Ala Lys Tyr Val Gly Lys Pro Met Asn Ser
                215                 220                 225 tac cct ctc ctc tcc ccc act ctc cca tcc cgc tca tca ctg gac ctc    1016
Tyr Pro Leu Leu Ser Pro Thr Leu Pro Ser Arg Ser Ser Leu Asp Leu
            230                 235                 240 ggc gtc ggc gga ttc ggc ctt cac tct ccc aca atg ggc ggc gac atg    1064
```

```
                Gly Val Gly Gly Phe Gly Leu His Ser Pro Thr Met Gly Gly Asp Met
                        245                 250                 255 ttt tcc cca gcc gag cta ctg cgg tcc gtc gcc ggc caa ccg gag gtc      1112
Phe Ser Pro Ala Glu Leu Leu Arg Ser Val Ala Gly Gln Pro Glu Val
        260                 265                 270 gac aag cca atg gtt atc gaa ctg gcg gtt gca gcc atg gaa gag ctg      1160
Asp Lys Pro Met Val Ile Glu Leu Ala Val Ala Ala Met Glu Glu Leu
275                 280                 285                 290 atc agg atg gct cag ctg ggg gaa ccg ctg tgg act agc agt cct ggt      1208
Ile Arg Met Ala Gln Leu Gly Glu Pro Leu Trp Thr Ser Ser Pro Gly
                295                 300                 305 ttg gat gga ggt aat gag att ctg aat gaa gag gag tat gtg cag aat      1256
Leu Asp Gly Gly Asn Glu Ile Leu Asn Glu Glu Glu Tyr Val Gln Asn
        310                 315                 320 ttt ccg aga ggg att ggg ccg aag ccg ttt gga ttg aag tcg gag gcg      1304
Phe Pro Arg Gly Ile Gly Pro Lys Pro Phe Gly Leu Lys Ser Glu Ala
        325                 330                 335 tcg agg gag acg gcc gtg gtg atc atg agt cat gtt aat ttg gtt gag      1352
Ser Arg Glu Thr Ala Val Val Ile Met Ser His Val Asn Leu Val Glu
        340                 345                 350 att ctc atg gat gcg aat caa tgg tcg aca atg ttc tcc ggc att gta      1400
Ile Leu Met Asp Ala Asn Gln Trp Ser Thr Met Phe Ser Gly Ile Val
355                 360                 365                 370 tcg agg ggt atg act ctt gag gta cta tca act ggt gtg gct gga aac      1448
Ser Arg Gly Met Thr Leu Glu Val Leu Ser Thr Gly Val Ala Gly Asn
                375                 380                 385 tac aat ggt gca ctg caa gtg atg aca gct gaa ttc caa gtt cca tct      1496
Tyr Asn Gly Ala Leu Gln Val Met Thr Ala Glu Phe Gln Val Pro Ser
        390                 395                 400 cct ctc gtt cca act cgc gaa agc tac ttc gtt aga tac tgc aaa caa      1544
Pro Leu Val Pro Thr Arg Glu Ser Tyr Phe Val Arg Tyr Cys Lys Gln
        405                 410                 415 cat ccg gac gga act tgg gcg gtc gtc gac gtc tcc ttg gac agt ctt      1592
His Pro Asp Gly Thr Trp Ala Val Val Asp Val Ser Leu Asp Ser Leu
420                 425                 430 cgc ccg agc agt ctt atg atg aga tgc cga aga agg cct tca gga tgt      1640
Arg Pro Ser Ser Leu Met Met Arg Cys Arg Arg Arg Pro Ser Gly Cys
435                 440                 445                 450 ttg ata caa gaa atg cca aat ggc tac tct aag gtg att tgg gta gaa      1688
Leu Ile Gln Glu Met Pro Asn Gly Tyr Ser Lys Val Ile Trp Val Glu
                455                 460                 465 cat ttt gaa gtt gat gat agg tct gtt cat agt atc tac aag cca ttg      1736
His Phe Glu Val Asp Asp Arg Ser Val His Ser Ile Tyr Lys Pro Leu
        470                 475                 480 gtg aac tct ggc att gca ttt ggg gcc aaa agg tgg gtt tct act ttg      1784
Val Asn Ser Gly Ile Ala Phe Gly Ala Lys Arg Trp Val Ser Thr Leu
        485                 490                 495 gat cga cag tgc gaa cgc ctt gca agt gtc atg gct agt agc att cca      1832
Asp Arg Gln Cys Glu Arg Leu Ala Ser Val Met Ala Ser Ser Ile Pro
                500                 505                 510 tcg gga gaa att gga gtg ata aca aca tcg gag ggg aga aag agc atg      1880
Ser Gly Glu Ile Gly Val Ile Thr Thr Ser Glu Gly Arg Lys Ser Met
515                 520                 525                 530 ctg aag cta gca gag aga atg gtg ctt agc ttt tgt gga ggg gtg agt      1928
Leu Lys Leu Ala Glu Arg Met Val Leu Ser Phe Cys Gly Gly Val Ser
                535                 540                 545 gct tca acc act cat caa tgg acg acg tta tct gga agc ggc gct gaa      1976
Ala Ser Thr Thr His Gln Trp Thr Thr Leu Ser Gly Ser Gly Ala Glu
        550                 555                 560
```

| | | | | | | | | | | | | | | | | |
|---|---|---|---|---|---|---|---|---|---|---|---|---|---|---|---|---|
| gat | gtg | agg | gtg | atg | acc | aga | aaa | agt | gta | gac | gat | ccg | ggc | agg | ccc | 2024 |
| Asp | Val | Arg | Val | Met | Thr | Arg | Lys | Ser | Val | Asp | Asp | Pro | Gly | Arg | Pro | |
| | | 565 | | | | 570 | | | | 575 | | | | | | |
| cct | ggt | att | gtt | ctg | aat | gct | gca | act | tca | ttc | tgg | ctt | cct | gtg | tct | 2072 |
| Pro | Gly | Ile | Val | Leu | Asn | Ala | Ala | Thr | Ser | Phe | Trp | Leu | Pro | Val | Ser | |
| | 580 | | | | | 585 | | | | | 590 | | | | | |
| cca | aaa | agg | gtt | ttt | gat | ttc | ctc | cgt | gat | gag | agt | tct | cgt | agc | gag | 2120 |
| Pro | Lys | Arg | Val | Phe | Asp | Phe | Leu | Arg | Asp | Glu | Ser | Ser | Arg | Ser | Glu | |
| 595 | | | | | 600 | | | | | 605 | | | | | 610 | |
| tgg | gat | atc | ctc | tcg | aac | gga | gga | gta | gtt | cag | gaa | atg | gct | cat | atc | 2168 |
| Trp | Asp | Ile | Leu | Ser | Asn | Gly | Gly | Val | Val | Gln | Glu | Met | Ala | His | Ile | |
| | | | | 615 | | | | | 620 | | | | | 625 | | |
| gcc | aat | ggt | cga | gat | cat | ggc | aac | tgt | gtt | tct | ctt | ctc | cgt | gtc | aat | 2216 |
| Ala | Asn | Gly | Arg | Asp | His | Gly | Asn | Cys | Val | Ser | Leu | Leu | Arg | Val | Asn | |
| | | 630 | | | | | 635 | | | | | 640 | | | | |
| agc | aca | aat | tca | aac | caa | agc | aac | atg | ctg | ata | ctc | caa | gag | agc | tgc | 2264 |
| Ser | Thr | Asn | Ser | Asn | Gln | Ser | Asn | Met | Leu | Ile | Leu | Gln | Glu | Ser | Cys | |
| | 645 | | | | | 650 | | | | | 655 | | | | | |
| act | gat | ccc | aca | ggc | tct | tat | gtg | ata | tat | gct | cct | gtg | gat | gtg | gtt | 2312 |
| Thr | Asp | Pro | Thr | Gly | Ser | Tyr | Val | Ile | Tyr | Ala | Pro | Val | Asp | Val | Val | |
| 660 | | | | | 665 | | | | | 670 | | | | | | |
| gcc | atg | aat | gtg | gtt | ctc | aat | gga | gga | gat | ccc | gac | tat | gtg | gct | ctc | 2360 |
| Ala | Met | Asn | Val | Val | Leu | Asn | Gly | Gly | Asp | Pro | Asp | Tyr | Val | Ala | Leu | |
| 675 | | | | 680 | | | | | 685 | | | | | 690 | | |
| ttg | cct | tca | ggt | ttc | gcc | atc | ctt | cct | gat | ggc | tcg | aat | ggg | gtt | cat | 2408 |
| Leu | Pro | Ser | Gly | Phe | Ala | Ile | Leu | Pro | Asp | Gly | Ser | Asn | Gly | Val | His | |
| | | | | 695 | | | | | 700 | | | | | 705 | | |
| ggt | ggt | gga | agt | gga | atc | ggt | gag | gtt | gga | tct | ggt | ggt | ggt | tct | ctg | 2456 |
| Gly | Gly | Gly | Ser | Gly | Ile | Gly | Glu | Val | Gly | Ser | Gly | Gly | Gly | Ser | Leu | |
| | | 710 | | | | | 715 | | | | | 720 | | | | |
| ctt | aca | gtt | gca | ttc | cag | ata | ttg | gtt | gat | tca | ata | cca | aca | gca | aag | 2504 |
| Leu | Thr | Val | Ala | Phe | Gln | Ile | Leu | Val | Asp | Ser | Ile | Pro | Thr | Ala | Lys | |
| | | 725 | | | | | 730 | | | | | 735 | | | | |
| ctg | tca | ctt | ggt | tct | gtt | gcg | acg | gtt | aac | agc | cta | att | gct | tgc | act | 2552 |
| Leu | Ser | Leu | Gly | Ser | Val | Ala | Thr | Val | Asn | Ser | Leu | Ile | Ala | Cys | Thr | |
| | 740 | | | | | 745 | | | | | 750 | | | | | |
| gtg | gaa | agg | atc | aag | gct | gca | gta | acg | ggg | gaa | agt | ccc | caa | tga | | 2597 |
| Val | Glu | Arg | Ile | Lys | Ala | Ala | Val | Thr | Gly | Glu | Ser | Pro | Gln | * | | |
| 755 | | | | 760 | | | | | 765 | | | | | | | | gcctaagggc tcctacaaat caatggaatt gaagaggact aagcttcaga gggagcaatg 2657 ggatcaatta ctggacgtcg gaagtagtca agaacgcacc tcagacaatc cttgccacgt 2717 ggcgtgtttc tgtagttctt aaaatagagc ttaaatgtag agcactccac catgcaaggg 2777 tgttggttcg ggtattgact cccccttcct atttgttatt ccctccctc tctctttgta 2837 cttctgcaga caagaagaaa aaaaacttgt tttagcttct attagtagct ctctttctct 2897 ctctagaatt ccctctctct ctctctctac tagattgatc accaacatat ataaacttca 2957 tcaaatttgt gcattatcat cccatgttga agtattttgt gagggatttc atttggtaaa 3017 atcagtattt ttttctttta taaatttaca aacatttcat tcc 3060

<210> SEQ ID NO 10
<211> LENGTH: 768
<212> TYPE: PRT
<213> ORGANISM: Phalaenopsis sp.

<400> SEQUENCE: 10

Met Leu Ala Gly Val Met Ile Pro Ala Arg Gln Val Pro Ser Met Ile
1               5                   10                  15

-continued

```
Gly Arg Asn Ser Ser Ala Leu Thr Leu Ala Gln Ile Asn Ile Leu Glu
             20                  25                  30

Gly Gln Gln Leu Pro Leu Gln His Gln Leu Ala Glu Leu Thr Ala Gln
         35                  40                  45

Ala Thr Thr Thr Ala Glu Ser Asp Met Met Arg Ala Arg Glu Asp Asp
 50                  55                  60

Phe Glu Ser Lys Ser Gly Ser Asp Asn Ile Glu Gly Gly Ser Gly Asp
 65                  70                  75                  80

Glu His Asp Pro Asn Gln Arg Pro Arg Lys Lys Arg Tyr His Arg His
                 85                  90                  95

Thr Gln His Gln Ile Gln Glu Met Glu Ala Phe Phe Lys Glu Cys Pro
            100                 105                 110

His Pro Asp Asp Lys Gln Arg Lys Ala Leu Ser Lys Glu Leu Gly Leu
            115                 120                 125

Glu Pro Leu Gln Val Lys Phe Trp Phe Gln Asn Lys Arg Thr Gln Met
130                 135                 140

Lys Thr Gln His Asp Arg Gln Glu Asn Ser Gln Leu Arg Ala Glu Asn
145                 150                 155                 160

Asp Lys Leu Arg Asn Glu Asn Leu Arg Tyr Lys Glu Ala Leu Ser Asn
                165                 170                 175

Ala Ser Cys Pro Asn Cys Gly Gly Pro Ala Thr Leu Gly Glu Met Ser
            180                 185                 190

Phe Asp Glu His His Leu Arg Ile Glu Asn Ala Arg Leu Arg Glu Glu
            195                 200                 205

Ile Asp Arg Ile Ser Gly Ile Ala Ala Lys Tyr Val Gly Lys Pro Met
210                 215                 220

Asn Ser Tyr Pro Leu Leu Ser Pro Thr Leu Pro Ser Arg Ser Ser Leu
225                 230                 235                 240

Asp Leu Gly Val Gly Gly Phe Gly Leu His Ser Pro Thr Met Gly Gly
                245                 250                 255

Asp Met Phe Ser Pro Ala Glu Leu Leu Arg Ser Val Ala Gly Gln Pro
            260                 265                 270

Glu Val Asp Lys Pro Met Val Ile Glu Leu Ala Val Ala Ala Met Glu
            275                 280                 285

Glu Leu Ile Arg Met Ala Gln Leu Gly Glu Pro Leu Trp Thr Ser Ser
290                 295                 300

Pro Gly Leu Asp Gly Gly Asn Glu Ile Leu Asn Glu Glu Tyr Val
305                 310                 315                 320

Gln Asn Phe Pro Arg Gly Ile Gly Pro Lys Pro Phe Gly Leu Lys Ser
                325                 330                 335

Glu Ala Ser Arg Glu Thr Ala Val Val Ile Met Ser His Val Asn Leu
            340                 345                 350

Val Glu Ile Leu Met Asp Ala Asn Gln Trp Ser Thr Met Phe Ser Gly
            355                 360                 365

Ile Val Ser Arg Gly Met Thr Leu Glu Val Leu Ser Thr Gly Val Ala
370                 375                 380

Gly Asn Tyr Asn Gly Ala Leu Gln Val Met Thr Ala Glu Phe Gln Val
385                 390                 395                 400

Pro Ser Pro Leu Val Pro Thr Arg Glu Ser Tyr Phe Val Arg Tyr Cys
                405                 410                 415

Lys Gln His Pro Asp Gly Thr Trp Ala Val Val Asp Val Ser Leu Asp
            420                 425                 430

Ser Leu Arg Pro Ser Ser Leu Met Met Arg Cys Arg Arg Arg Pro Ser
```

-continued

```
                435                 440                 445
Gly Cys Leu Ile Gln Glu Met Pro Asn Gly Tyr Ser Lys Val Ile Trp
    450                 455                 460
Val Glu His Phe Glu Val Asp Asp Arg Ser Val His Ser Ile Tyr Lys
465                 470                 475                 480
Pro Leu Val Asn Ser Gly Ile Ala Phe Gly Ala Lys Arg Trp Val Ser
                485                 490                 495
Thr Leu Asp Arg Gln Cys Glu Arg Leu Ala Ser Val Met Ala Ser Ser
                500                 505                 510
Ile Pro Ser Gly Glu Ile Gly Val Ile Thr Thr Ser Glu Gly Arg Lys
        515                 520                 525
Ser Met Leu Lys Leu Ala Glu Arg Met Val Leu Ser Phe Cys Gly Gly
    530                 535                 540
Val Ser Ala Ser Thr Thr His Gln Trp Thr Thr Leu Ser Gly Ser Gly
545                 550                 555                 560
Ala Glu Asp Val Arg Val Met Thr Arg Lys Ser Val Asp Pro Gly
                565                 570                 575
Arg Pro Pro Gly Ile Val Leu Asn Ala Ala Thr Ser Phe Trp Leu Pro
                580                 585                 590
Val Ser Pro Lys Arg Val Phe Asp Phe Leu Arg Asp Glu Ser Ser Arg
        595                 600                 605
Ser Glu Trp Asp Ile Leu Ser Asn Gly Gly Val Val Gln Glu Met Ala
    610                 615                 620
His Ile Ala Asn Gly Arg Asp His Gly Asn Cys Val Ser Leu Leu Arg
625                 630                 635                 640
Val Asn Ser Thr Asn Ser Asn Gln Ser Asn Met Leu Ile Leu Gln Glu
                645                 650                 655
Ser Cys Thr Asp Pro Thr Gly Ser Tyr Val Ile Tyr Ala Pro Val Asp
                660                 665                 670
Val Val Ala Met Asn Val Val Leu Asn Gly Gly Asp Pro Asp Tyr Val
        675                 680                 685
Ala Leu Leu Pro Ser Gly Phe Ala Ile Leu Pro Asp Gly Ser Asn Gly
    690                 695                 700
Val His Gly Gly Gly Ser Gly Ile Gly Glu Val Gly Ser Gly Gly Gly
705                 710                 715                 720
Ser Leu Leu Thr Val Ala Phe Gln Ile Leu Val Asp Ser Ile Pro Thr
                725                 730                 735
Ala Lys Leu Ser Leu Gly Ser Val Ala Thr Val Asn Ser Leu Ile Ala
                740                 745                 750
Cys Thr Val Glu Arg Ile Lys Ala Ala Val Thr Gly Glu Ser Pro Gln
        755                 760                 765
```